(12) United States Patent
Arora et al.

US010787424B2

(10) Patent No.: US 10,787,424 B2
(45) Date of Patent: *Sep. 29, 2020

(54) OXOPIPERAZINE HELIX MIMETICS FOR CONTROL OF HYPOXIA-INDUCIBLE GENE EXPRESSION

(71) Applicant: NEW YORK UNIVERSITY, New York, NY (US)

(72) Inventors: Paramjit S. Arora, Cold Spring Harbor, NY (US); Brooke Bullock Lao, Leesville, SC (US); Richard Bonneau, New York, NY (US); Kevin Drew, Austin, TX (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/312,875

(22) PCT Filed: May 20, 2015

(86) PCT No.: PCT/US2015/031816
§ 371 (c)(1),
(2) Date: Nov. 21, 2016

(87) PCT Pub. No.: WO2015/179547
PCT Pub. Date: Nov. 26, 2015

(65) Prior Publication Data
US 2017/0190673 A1 Jul. 6, 2017

Related U.S. Application Data

(60) Provisional application No. 62/001,530, filed on May 21, 2014.

(51) Int. Cl.
*C07D 241/08* (2006.01)
*C07C 29/88* (2006.01)
*C07C 29/80* (2006.01)

(52) U.S. Cl.
CPC ............ *C07D 241/08* (2013.01); *C07C 29/80* (2013.01); *C07C 29/88* (2013.01)

(58) Field of Classification Search
CPC ........ C07D 241/08; C07C 29/80; C07C 29/88
See application file for complete search history.

(56) References Cited

U.S. PATENT DOCUMENTS

| 8,791,121 | B2 | 7/2014 | Arora et al. |
| 9,255,086 | B2 | 2/2016 | Arora et al. |
| 9,309,230 | B2 | 2/2016 | Arora et al. |
| 9,624,203 | B2 | 4/2017 | Arora et al. |
| 9,695,153 | B2 | 7/2017 | Arora et al. |
| 9,783,526 | B2 | 10/2017 | Arora et al. |
| 2003/0191049 | A1 | 10/2003 | Amblard et al. |
| 2005/0101588 | A1 | 5/2005 | Grant et al. |
| 2012/0040992 | A1 | 2/2012 | Arora et al. |
| 2014/0205655 | A1 | 7/2014 | Arora et al. |
| 2015/0018364 | A1 | 1/2015 | Arora et al. |
| 2015/0072991 | A1 | 3/2015 | Arora et al. |
| 2016/0214965 | A1 | 7/2016 | Arora et al. |
| 2016/0297802 | A1 | 10/2016 | Arora et al. |
| 2017/0037033 | A1* | 2/2017 | Arora .................. C07D 403/14 |

FOREIGN PATENT DOCUMENTS

| JP | 2003-519629 | | 6/2003 | |
| WO | 96/20173 | A1 | 7/1996 | |
| WO | 2001/051506 | A2 | 7/2001 | |
| WO | 2012/02114 | A1 | 2/2012 | |
| WO | WO 2012/021144 | * | 2/2012 | ........... C07D 403/06 |
| WO | 2013/123511 | A1 | 8/2013 | |
| WO | WO 2013/123511 | * | 8/2013 | ........... C07D 401/12 |
| WO | WO 2015/160914 | * | 10/2015 | ........... A61K 31/496 |

OTHER PUBLICATIONS

Xin, et al, Evaluating minimalist mimics by exploring key orientations on secondary structures (EKOS), Organic & Biomolecular Chemistry, 11(44), 7789-7801 (2013).*
Dames et al., "Structural Basis for Hif-1 α/CBP Recognition in the Cellular Hypoxic Response," Proc. Nat'l Acad. Sci. 99:5271-76 (2002).
Extended European Search Report for European Patent Application No. 13749783.0 (dated Sep. 30, 2015).
Freedman et al., "Structural Basis for Recruitment of CBP/p300 by Hypoxia-Inducible Factor-1α," Proc. Nat'l Acad. Sci. 99(8):5367-72 (2002).
Hirota & Semenza, "Regulation of Angiogenesis by Hypoxia-Inducible Factor 1," Crit. Rev. Oncol./Hematol. 59:15-26 (2006).
International Search Report and Written Opinion for corresponding Application No. PCT/US2015/031816 (dated Dec. 7, 2015).
International Search Report and Written Opinion for PCT/US2013/026722 (dated Jul. 1, 2013).
Raghuraman et al., "Expanding the Scope of Oligo-Pyrrolinone-Pyrrolidines as Protein-Protein Interface Mimics," J. Org. Chem. 78(10):4823-33 (2013).
Semenza, "Targeting HIF-1 for Cancer Therapy," Nat. Rev. Cancer 3:721-32 (2003).
Tošovská & Arora, "Oligooxopiperazines as Nonpeptidic Alpha-Helix Mimetics," Org. Lett. 12:1588-91 (2010).
PCT/US2015/031816, International Preliminary Report on Patentability (dated Dec. 1, 2016).
Lau et al., "Rational Design of Topographical Helix Mimics as Potent Inhibitors of Protein—Protein Interactions," J. Am. Chem. Soc. 136:7877-88 (2014).
European Patent Application No. 15795595.6, Extended European Search Report (dated Oct. 9, 2017).

* cited by examiner

*Primary Examiner* — Erich A Leeser
(74) *Attorney, Agent, or Firm* — Troutman Pepper Hamilton Sanders LLP (Rochester)

(57) ABSTRACT

The present invention relates to oxopiperazines that mimic helix αB of the C-terminal transactivation domain of HIF1α. Also disclosed are pharmaceutical compositions containing these oxopiperazines and methods of using these oxopiperazines (e.g., to reduce gene transcription, treat or prevent disorders mediated by interaction of HIF1a with CREB-binding protein and/or p300, reduce or prevent angiogenesis in a tissue, induce apoptosis, and decrease cell survival and/or proliferation).

23 Claims, 10 Drawing Sheets
Specification includes a Sequence Listing.

Figures 1A–B

A  P300 TAZ1
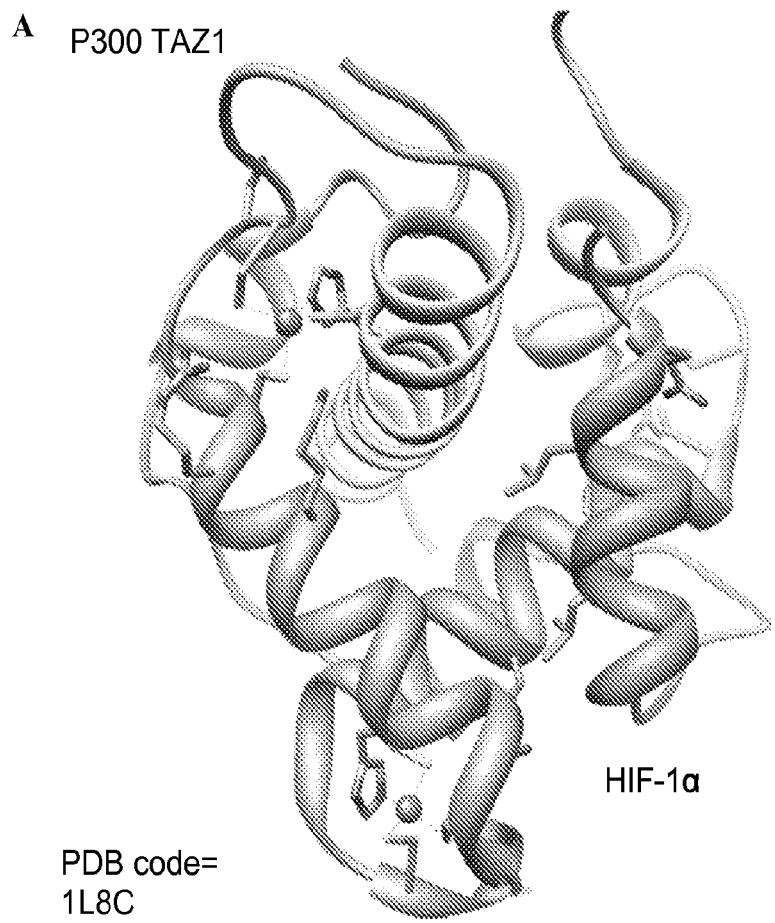
PDB code=
1L8C
HIF-1α
B
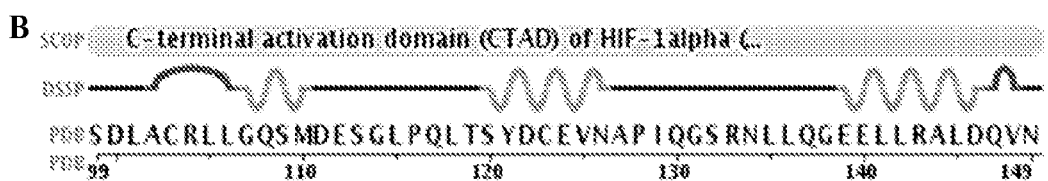
C
| Residue | Helix residue | PDB residue | Helix position | ΔΔG (kcal/mol) |
|---|---|---|---|---|
| Leu | 818 | 141 | $i$ | 2.4 |
| Leu | 822 | 145 | $i+4$ | 2.2 |
| Gln | 824 | 147 | $i+6$ | 1.3 |
Figures 3A–C

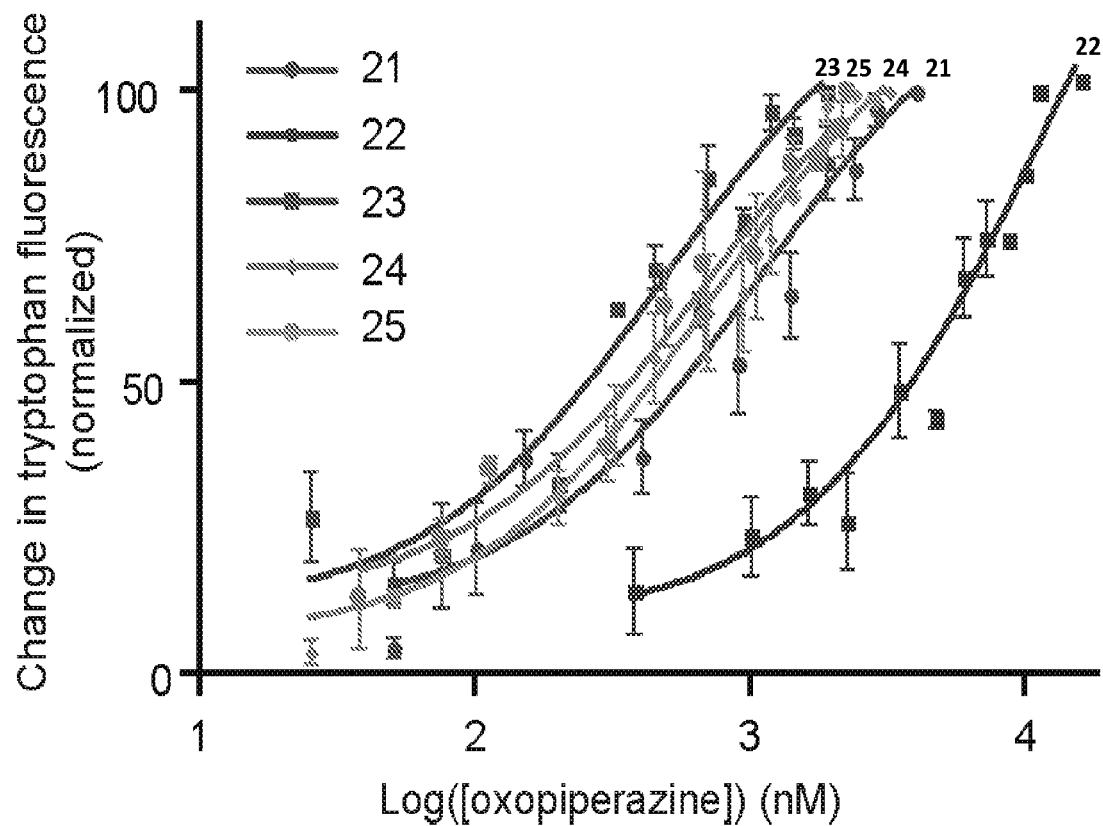
Figure 8
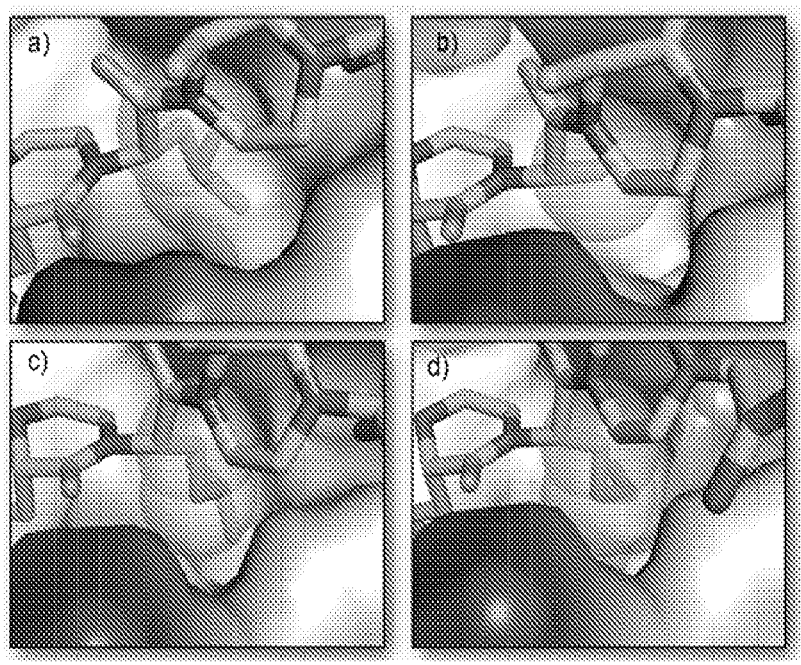
Figures 9A–D

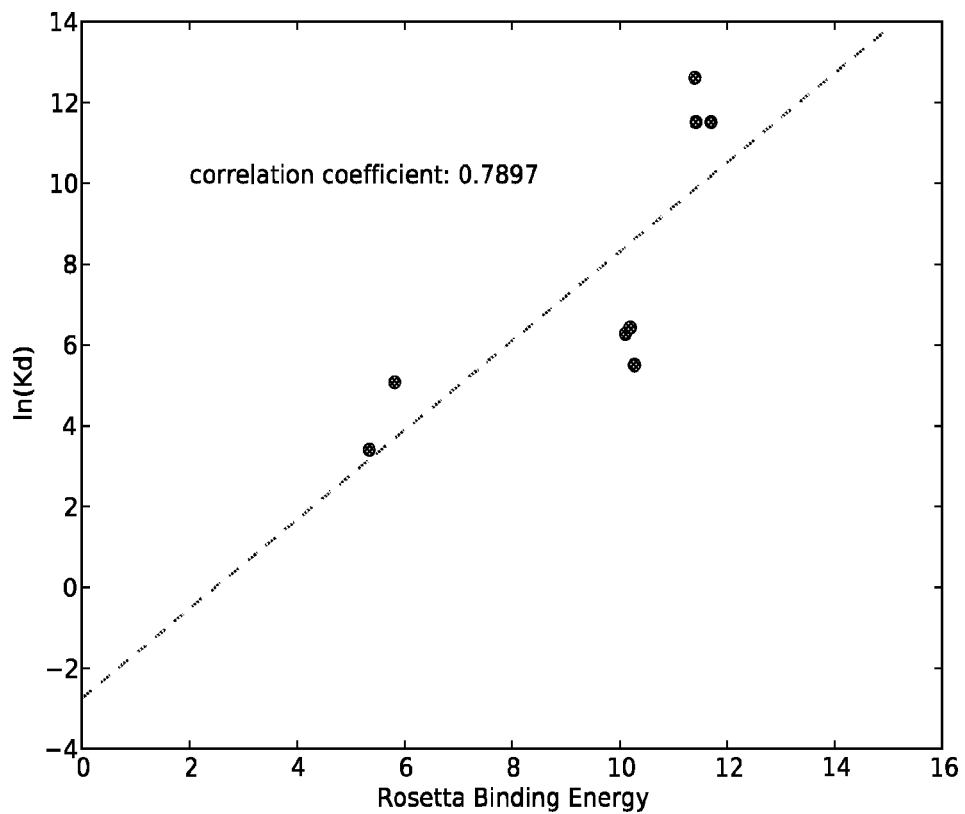
Figure 10
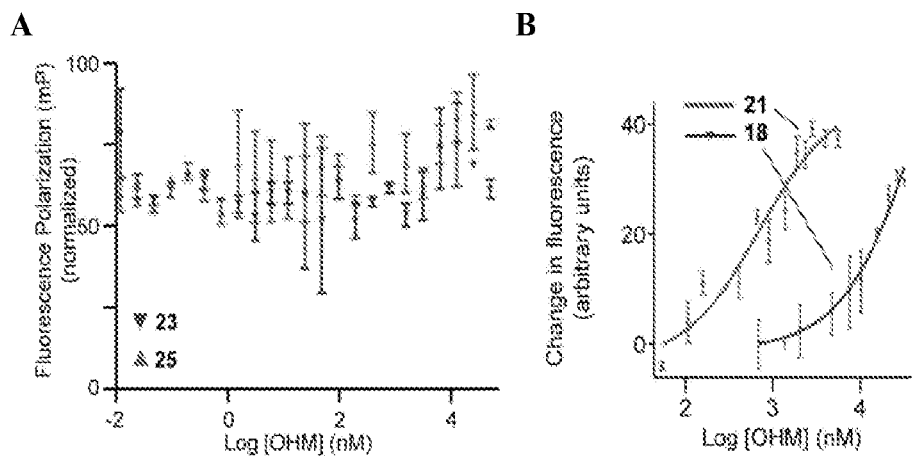
Figures 11A–B

Oxopiperazine helix mimetic 18: F(3-Cl)WFL-NH₂

SEQUENCE LISTING

```
<160> NUMBER OF SEQ ID NOS: 5

<210> SEQ ID NO 1
<211> LENGTH: 51
<212> TYPE: PRT
<213> ORGANISM: Artificial
<220> FEATURE:
<223> OTHER INFORMATION: Human HIF1alpha C-terminal transactivation
      domain

<400> SEQUENCE: 1

Ser Asp Leu Ala Cys Arg Leu Leu Gly Gln Ser Met Asp Glu Ser Gly
1               5                   10                  15

Leu Pro Gln Leu Thr Ser Tyr Asp Cys Glu Val Asn Ala Pro Ile Gln
            20                  25                  30

Gly Ser Arg Asn Leu Leu Gln Gly Glu Glu Leu Leu Arg Ala Leu Asp
        35                  40                  45

Gln Val Asn
    50

<210> SEQ ID NO 2
<211> LENGTH: 29
<212> TYPE: PRT
<213> ORGANISM: Artificial
<220> FEATURE:
<223> OTHER INFORMATION: Signal peptide

<400> SEQUENCE: 2

Met Met Ser Phe Val Ser Leu Leu Leu Val Gly Ile Leu Phe Tyr Ala
1               5                   10                  15

Thr Glu Ala Glu Gln Leu Thr Lys Cys Glu Val Phe Gln
            20                  25
```

```
<210> SEQ ID NO 3
<211> LENGTH: 4
<212> TYPE: PRT
<213> ORGANISM: Artificial
<220> FEATURE:
<223> OTHER INFORMATION: ER retention signal

<400> SEQUENCE: 3

Lys Glu Asp Leu
1

<210> SEQ ID NO 4
<211> LENGTH: 8
<212> TYPE: PRT
<213> ORGANISM: Artificial
<220> FEATURE:
<223> OTHER INFORMATION: Nuclear transport peptide

<400> SEQUENCE: 4

Pro Pro Lys Lys Lys Arg Lys Val
1               5

<210> SEQ ID NO 5
<211> LENGTH: 25
<212> TYPE: PRT
<213> ORGANISM: Artificial
<220> FEATURE:
<223> OTHER INFORMATION: Transport peptide

<400> SEQUENCE: 5

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25
```

OXOPIPERAZINE HELIX MIMETICS FOR CONTROL OF HYPOXIA-INDUCIBLE GENE EXPRESSION

This application is a national stage application under 35 U.S.C. § 371 of International Application No. PCT/US2015/031816, filed May 20, 2015, which claims the benefit of U.S. Provisional Patent Application Ser. No. 62/001,530, filed May 21, 2014, which is hereby incorporated by reference in its entirety.

This invention was made with government support under CHE-1151554 awarded by National Science Foundation and RC4-AI092765, PN2-EY016586, IU54CA143907-01, and EY016586-06 awarded by National Institutes of Health. The government has certain rights in the invention.

FIELD OF THE INVENTION

The present invention relates to oxopiperazines that substantially mimic helix αB of the C-terminal transactivation domain of Hypoxia-Inducible Factor 1α.

BACKGROUND OF THE INVENTION

Protein-protein interactions are often mediated by amino acid residues organized on secondary structures (Jones & Thornton, *Prog. Biophys. Mol. Bio.* 63:31 (1995)). Designed oligomeric ligands that can mimic the array of protein-like functionality at interfaces offer an attractive approach to target therapeutically important interactions (Ko et al., *Chem. Soc. Rev.* 40:4411 (2011)). Efforts to mimic interfacial α-helices have resulted in three overarching synthetic strategies: helix stabilization, helical foldamers, and helical surface mimetics (Azzarito et al., *Nat. Chem.* 5:161 (2013); Henchey et al., *Curr. Opin. Chem. Biol.* 12:692 (2008)).

Helix stabilization employs side chain crosslinks (Schafmeister et al., *J. Am. Chem. Soc.* 122:5891 (2000); Harrison et al., *Proc. Nat'l Acad. Sci. U.S.A.* 107:11686 (2010)) or hydrogen-bond surrogates (Patgiri et al., *Acc. Chem. Res.* 41:1289 (2008)) to preorganize amino acid residues and initiate helix formation. Helical foldamers are nonnatural oligomers that adopt defined helical conformations (Gellman, *Acc. Chem. Res.* 31:173 (1998); Goodman et al., *Nat. Chem. Biol.* 3:252 (2007)). Prominent examples include β-peptide (Cheng et al., *Chem. Rev.* 101:3219 (2001); Horne & Gellman, *Acc. Chem. Res.* 41:1399 (2008); Seebach & Gardiner, *Acc. Chem. Res.* 41:1366 (2008)) and peptoid helices (Yoo & Kirshenbaum, *Curr. Opin. Chem. Biol.* 12:714 (2008)). Helical surface mimetics utilize conformationally restricted scaffolds with attached functional groups that mimic the topography of α-helical side chains. With the exception of some elegant examples (Marimganti et al., *Org. Lett.* 11:4418 (2009); Jayatunga et al., *Biorg. Med. Chem. Lett.* 24:717 (2014); Thompson & Hamilton, *Org. Biomol. Chem.* 10:5780 (2012); Thompson et al., *Tetrahedron* 68:4501 (2012); Jung et al., *Org. Lett.* 15:3234 (2013)), surface mimetics typically impart functionality from one face of the helix (Marimganti et al., *Org. Lett.* 11:4418 (2009)), while stabilized peptide helices and foldamers are able to reproduce functionality present on multiple faces of the target helix. A key advantage of helix surface mimicry is that it affords low molecular weight compounds as modulators of protein interactions (Plante et al., *Chem. Commun.* 5091 (2009); Shaginian et al., *J. Am. Chem. Soc.* 131:5564 (2009); Restorp & Rebek, *Bioorg. Med. Chem. Lett.* 18:5909 (2008); Tošovská & Arora, *Org. Lett.* 12:1588 (2010); Buhrlage et al., *ACS Chem. Biol.* 4:335 (2009); Lee et al., *J. Am. Chem. Soc.* 133:676 (2011)).

A recent survey of protein-protein complexes in the Protein Data Bank (PDB) suggests that a significant portion of interface helices use one face to target the binding partner (Bullock et al., *J. Am. Chem. Soc.* 133:14220 (2011); Jochim & Arora, *ACS Chem. Biol.* 5:919 (2010)). This analysis points to the meaningful role that topographical helix mimics can play in affording small molecule inhibitors of protein-protein interactions. The classical examples of helix surface mimics were described by Hamilton et al. (Cummings & Hamilton, *Curr. Opin. Chem. Biol.* 14:341 (2010); Yin & Hamilton, *Angew. Chem. Int'l Ed.* 44:4130 (2005); Orner et al., *J. Am. Chem. Soc.* 123:5382 (2001), and contained aromatic scaffolds displaying protein-like functionality (Azzarito et al., *J. Nat. Chem.* 5:161 (2013)). Oxopiperazines have since been proposed as a new class of helix mimetics (FIGS. 1A-B) (Tošovská & Arora, *Org. Lett.* 12:1588 (2010)). Oxopiperazine-based scaffolds offer chiral backbones and can be easily assembled from α-amino acids allowing rapid diversification of the scaffold. 2-oxopiperazines and diketopiperazines have a rich history in medicinal chemistry (Tošovská & Arora, *Org. Lett.* 12:1588 (2010); Gante, *Angew. Chem. Intl Ed. Engl.* 33:1699 (1994); Giannis & Kolter, *Angew. Chem. Int'l Ed.* 32:1244 (1993); Herrero et al., *J. Org. Chem.* 67:3866 (2002); Kitamura et al., *J. Med. Chem.* 44:2438 (2001); Sugihara et al., *J. Med. Chem.* 41:489 (1998); Borthwick et al., *J. Med. Chem.* 49:4159 (2006).

As illustrated in FIG. 2, angiogenesis, the induction of new blood vessels, is critical for normal growth as well as pathogenesis of various disorders. In cancers, angiogenesis accelerates growth of solid tumors and provides a gateway to metastasis via the newly formed vasculature. In contrast, therapeutic angiogenesis is important for reducing the effects of tissue ischemia and preventing organ failure.

The process of angiogenesis is tightly controlled by a number of specific mitogens, among which vascular endothelial growth factor (VEGF) and its receptors play a key role. The levels of VEGF are upregulated across a broad range of tumors, and play a causal role in oncogenic signaling. In cells and tissues, transcription of VEGF gene is regulated by hypoxia-inducible factors. Among them, Hypoxia-Inducible Factor 1 ("HIF1") is the main regulator of oxygen-dependent transcription in a majority of organs and accounts for the increase in expression of hypoxia-inducible genes.

HIF1 consists of an oxygen-sensitive α and a constitutively expressed β subunit. Under well-oxygenated conditions, HIF1α is hydroxylated (Ivan et al., *Science* 292:464-8 (2001)), ubiquitinated, and degraded by the ubiquitin-proteasome system. Under hypoxia, HIF1α is stabilized and translocates into the nucleus where heterodimerization with its constitutively expressed binding partner, aryl hydrocarbon receptor nuclear translocator ("ARNT") (Wood et al., *J. Biol. Chem.* 271:15117-23 (1996)), results in binding to a cognate hypoxia response element ("HRE") (Forsythe et al., *Mol. Cell. Biol.* 16:4604-13 (1996)). The heterodimer then recruits transcriptional coactivators, p300, CBP, and SRC-1, resulting in the upregulation of the hypoxia-inducible genes.

Regulation of the activity of hypoxia-inducible factors includes three critical steps: (i) inhibition of hydroxylation of two proline residues to preclude interaction of HIF1α with pVHL, a part of ubiquitin ligase complex, thereby preventing its proteasomal destruction; (ii) inhibition of hydroxylation of Asn803 by Factor Inhibiting HIF1α ("FIH") (Lando et al., *Genes Develop.* 16:1466-71 (2002))

to enable recruitment of coactivators, which trigger overexpression of hypoxia inducible genes, including genes encoding angiogenic peptides such as VEGF and VEGF receptors VEGFR-1 (Flt-1) and VEGFR-2 (KDR/Flk-1), as well as proteins involved in altered energy metabolism, such as the glucose transporters GLUT1 and GLUT3, and hexokinases 1 and 2 (Forsythe et al., *Mol. Cell. Biol.* 16:4604-13 (1996); Okino et al., *J. Biol. Chem.* 273:23837-43 (1998)); and (iii) interaction of promoter-bound HIF1α with coactivator protein p300 (or the homologous CREB binding protein, CBP) leading to upregulation of transcription.

The interaction between the cysteine-histidine rich 1 domain ("CH1") of p300/CBP and the C-terminal transactivation domain ("C-TAD$_{786-826}$") of HIF1α (Freedman et al., *Proc. Nat'l Acad. Sci. USA* 99:5367-72 (2002); Dames et al., *Proc. Nat'l Acad. Sci. USA* 99:5271-6 (2002)) mediates transactivation of hypoxia-inducible genes (Hirota & Semenza, *Crit. Rev. Oncol. Hematol.* 59:15-26 (2006); Semenza, *Nat. Rev. Cancer* 3:721-32 (2003)) (see FIG. 3A). As illustrated in FIGS. 3A-C, structural studies provide a molecular basis for this transcription factor-coactivator interaction and identify two short α-helical domains from HIF1α as key determinants for its recognition by p300 (Freedman et al., *Proc. Nat'l Acad. Sci. USA* 99:5367-72 (2002); Dames et al., *Proc. Nat'l Acad. Sci. U.S.A.* 99:5271-76 (2002)). Synthetic mimics of these domains could inhibit HIF1α/p300 or HIF1α/CBP complex formation and regulate transcription. Key residues contributing to the binding of one of the two helices (PDB code 1L8C, residues 139-147) are shown in FIG. 3C.

Because interaction of HIF1α C-TAD with transcriptional coactivator p300/CBP is a point of significant amplification in transcriptional response, its disruption with designed ligands could be an effective means of suppressing aerobic glycolysis and angiogenesis (i.e., the formation of new blood vessels) in cancers (Hirota & Semenza, *Crit. Rev. Oncol. Hematol.* 59:15-26 (2006); Ramanathan et al., *Proc. Nat'l Acad. Sci. USA* 102:5992-7 (2005); Underiner et al., *Curr. Med. Chem.* 11:731-45 (2004)).

The present invention is directed to overcoming these and other deficiencies in the art.

SUMMARY OF THE INVENTION

One aspect of the present invention relates to an oxopiperazine selected from the group consisting of
(i) Formula IA:

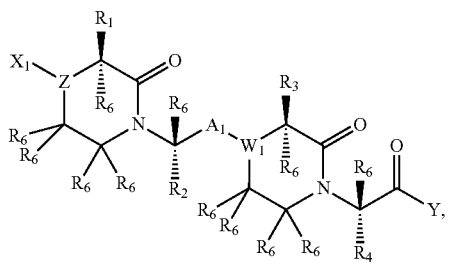

IA wherein:
$R_1$ is hydrophobic and is an amino acid side chain, OR, SR, an alkyl, or an aryl; wherein R is independently H, an alkyl, or an aryl;
$R_2$ is an amino acid side chain, OR, SR, an alkyl, or an aryl; wherein R is independently H, an alkyl, or an aryl; wherein $R_2$ is either a leucine side chain or longer than a leucine side chain by at least one backbone methylene; and with the proviso that $R_1$ and $R_2$ are not both an aryl;
$R_3$ is hydrophobic and is an amino acid side chain, SR, or an alkyl; wherein R is independently H, an alkyl, or an aryl;
$R_4$ is a hydrogen bond donor, a hydrophobic amino acid side chain, or an amide;
each $R_6$ is independently H, $N(R)_2$, OR, halogen, an alkyl, or an aryl; wherein each R is independently H, an alkyl, or an aryl;
$X_1$ is H, $N(R)_2$, OR, COR', $CO_2R'$, CONR', an alkyl, an aryl, an arylalkyl, a cycloalkyl, a heteroaryl, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;
Z is N, O, or S;
$A_1$-$W_1$ is:

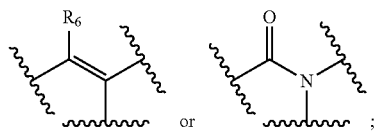

and
Y is OR', $N(R''')_2$, an alkyl, an aryl, an arylalkyl, a cycloalkyl, a heteroaryl, an amino acid, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag;
(ii) Formula IB:

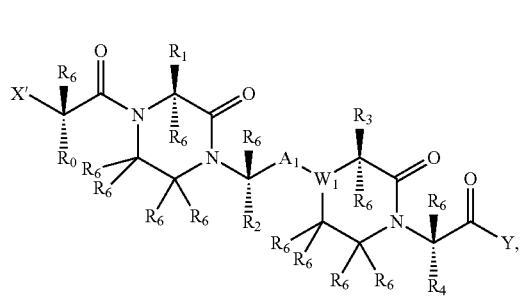

IB wherein:
$R_0$ is hydrophobic and is an amino acid side chain, OR, SR, an alkyl, or an aryl; wherein R is independently H, an alkyl, or an aryl;
$R_1$ and $R_2$ are each independently a solubilizing group, a hydrophobic amino acid side chain, H, $N(R)_2$, OR, SR, halogen, an alkyl, or an aryl; wherein each R is independently H, an alkyl, or an aryl;
$R_3$ is an amino acid side chain, OR, SR, an alkyl, or an aryl; wherein R is independently H, an alkyl, or an aryl; wherein $R_2$ is either a leucine side chain or longer than a leucine side chain by at least one backbone methylene; and with the proviso that $R_0$ and $R_3$ are not both an aryl;

$R_4$ is a hydrogen bond donor, a hydrophobic amino acid side chain, or an amide;

each $R_6$ is independently H, $N(R)_2$, OR, halogen, an alkyl, or an aryl; wherein each R is independently H, an alkyl, or an aryl;

X' is H, COR', $CO_2R'$, CONR', OR', $N(R'')_2$, an alkyl, an aryl, an arylalkyl, a cycloalkyl, a heteroaryl, a solubilizing group, a targeting moiety, or a tag; wherein R' is H, an alkyl, an aryl, an arylalkyl, a cycloalkyl, a heteroaryl, an amino acid residue, a peptide of 1 to about 10 amino acid residues, a targeting moiety, or a tag; and wherein each R'' is independently H, $CO_2R'$, CONR', an alkyl, an aryl, an arylalkyl, a cycloalkyl, a heteroaryl, a targeting moiety, or a tag;

$A_1$-$W_1$ is:

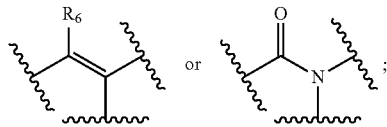

and

Y is OR', $N(R''')_2$, an alkyl, an aryl, an arylalkyl, a cycloalkyl, a heteroaryl, an amino acid, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag;

and (iii) Formula IC:

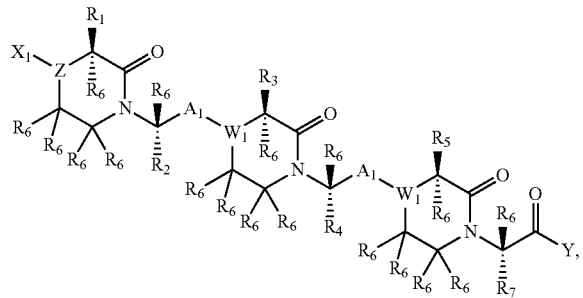

IC wherein:

$R_1$ is hydrophobic and is an amino acid side chain, OR, SR, an alkyl, or an aryl; wherein R is independently H, an alkyl, or an aryl;

$R_2$ is an amino acid side chain, OR, SR, an alkyl, or an aryl; wherein R is independently H, an alkyl, or an aryl; wherein $R_2$ is either a leucine side chain or longer than a leucine side chain by at least one backbone methylene; and with the proviso that $R_1$ and $R_2$ are not both an aryl;

$R_3$ is hydrophobic and is an amino acid side chain, SR, or an alkyl; wherein R is independently H, an alkyl, or an aryl;

$R_4$ is a hydrogen bond donor or an amide;

$R_5$ is a hydrophobic amino acid side chain;

each $R_6$ is independently H, $N(R)_2$, OR, halogen, an alkyl, or an aryl; wherein each R is independently H, an alkyl, or an aryl;

$R_7$ is a solubilizing group, a hydrophobic amino acid side chain, H, $N(R)_2$, OR, SR, halogen, an alkyl, or an aryl; wherein each R is independently H, an alkyl, or an aryl;

$X_1$ is H, $N(R)_2$, OR, COR', $CO_2R'$, CONR', an alkyl, an aryl, an arylalkyl, a cycloalkyl, a heteroaryl, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;

Z is N, O or S;

each $A_1$-$W_1$ is independently:

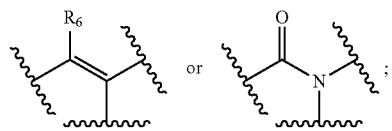

and

Y is OR', $N(R''')_2$, an alkyl, an aryl, an arylalkyl, a cycloalkyl, a heteroaryl, an amino acid, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag.

The present invention is further directed to pharmaceutical formulations containing the oxopiperazine of Formula IA, Formula IB, or Formula IC.

A second aspect of the present invention relates to a method of reducing transcription of a gene in a cell, where transcription of the gene is mediated by interaction of HIF1α with CREB-binding protein and/or p300. This method involves contacting the cell with an oxopiperazine of the present invention under conditions effective to reduce transcription of the gene.

A third aspect of the present invention relates to a method of treating or preventing in a subject a disorder mediated by interaction of HIF1α with CREB-binding protein and/or p300. This method involves administering an oxopiperazine of the present invention to the subject under conditions effective to treat or prevent the disorder.

A fourth aspect of the present invention relates to a method of reducing or preventing angiogenesis in a tissue. This method involves contacting the tissue with an oxopiperazine of the present invention under conditions effective to reduce or prevent angiogenesis in the tissue.

A fifth aspect of the present invention relates to a method of inducing apoptosis of a cell. This method involves contacting the cell with an oxopiperazine of the present invention under conditions effective to induce apoptosis of the cell.

A sixth aspect of the present invention relates to a method of decreasing survival and/or proliferation of a cell. This method involves contacting the cell with an oxopiperazine of the present invention under conditions effective to decrease survival and/or proliferation of the cell.

The potential of oxopiperazine helix mimetics (OHMs) to target protein-protein interactions was recently established in biochemical, cell culture, and in vivo assays (Lau et al., *Proc. Nat'l Acad. Sci.* 10.1073/pnas.1402393111 (published online May 14, 2014); International Patent Application No. PCT/US13/26722 to Arora et al., each of which is hereby incorporated by reference in its entirety). It was shown that OHMs that mimic a key α-helix from HIF1α can inhibit the interactions of this transcription factor with coactivator p300/CBP. Significantly, the designed compounds downregulate the expression of a specific set of genes and reduce tumor burden in mouse xenograft models. Encouraged by this success, it was sought to develop a computational approach to design and optimize oxopiperazine analogs with natural and nonnatural amino acid residues.

The objective of computational molecular design is to reduce the total number of possible designs to a manageable number that can be efficiently synthesized and experimentally tested. Contemporary computational methods for design of protein-protein interaction inhibitors often emphasize fragment-based screening (Schneider & Fechner, *Nat. Rev. Drug Discov.* 4:649 (2005); Winter et al., *Quart. Rev. Biophys.* 45:383 (2012), each of which is hereby incorporated by reference in its entirety). As a complementary approach, peptidomimetic design seeks to graft appropriate side chains on stable synthetic backbones, i.e., helical or β-sheet scaffolds.

The new computational protocol was used to develop nanomolar ligands for two different protein-protein interactions. Described herein is the design of oxopiperazine dimers that mimic HIF1α to develop ligands for p300/CBP. The previous design of oxopiperazine analogs of HIF1α was based on mimicry of natural residues and resulted in submicromolar inhibitors. As described herein, application of the new Rosetta based peptidomimetic design strategy with noncanonical residues affords oxopiperazine helix mimetics that are greater than an order of magnitude more potent than the scaffolds that displayed wild-type residues.

BRIEF DESCRIPTION OF THE DRAWINGS

FIG. 1A illustrates the design of amino acid-derived oxopiperazines (Tošovskaá& Arora, *Org. Lett.* 12:1588 (2010), which is hereby incorporated by reference in its entirety). The oxopiperazines are obtained by linking neighboring amide nitrogen atoms in peptides with ethylene bridges, as depicted. FIG. 1B is an overlay of an 8-mer canonical α-helix and an oxopiperazine dimer (left), and a predicted low energy structure of an oxopiperazine dimer (right). Side chain groups are depicted as spheres.

FIGS. 3A-C relate to the HIF1α/TAZ1 structure (Dames et al. *Proc. Nat'l Acad. Sci.* 99:5271 (2002), which is hereby incorporated by reference in its entirety). FIG. 3A is a schematic diagram illustrating the structure of the complex of the C-terminal transactivation domain ("C-TAD") of HIF1α with cysteine-histidine rich 1 domain ("CH1") of the coactivator protein p300. The human HIF1α C-TAD sequence (SEQ ID NO: 1) is shown in FIG. 3B, along with the location of the αA helix (PDB residues 121-127) and αB helix (PDB residues 139-147). FIG. 3C is a table showing the key residues contributing to the binding of helix αB.

FIG. 7 is an overlay of HIF1α helix$_{776-826}$ (in magenta) and OHM 21 in complex with the CH1 domain of p300/CBP (PDB code 1L8C). The $R_1$, $R_2$ and $R_4$ positions of OHM 21 access the same p300 molecular pockets as Leu818, Leu822, and Gln824 of the HIF1α C-terminal activation domain.

FIG. 8 is a graph of the binding affinity for p300-CH1 determined by tryptophan fluorescence spectroscopy. Binding curves for compounds OHM 21-25 are shown.

FIGS. 9A-D are space-filling models of the $R_2$ position of HIF OHM mimics in the p300-CH1 binding pocket, showing leucine of OHM 21 (FIG. 9A), alanine of OHM 22 (FIG. 9B), homoleucine of OHM 25 (FIG. 9C), and norleucine of OHM 23 (FIG. 9D). The space-filling model reveals that longer hydrophobic side chains form better packing in the p300-CH1 pocket, natively inhabited by the Leu822 of HIF1α.

FIG. 10 is a graph showing the correlation of Rosetta binding energy predictions with experimental $K_d$ for p300-CH1 ligands. Data points are taken from Table 8, and the correlation coefficient was calculated using Python's scipy.stats.stats.pearsonr function. Rosetta binding energy (x axis) approximates free energy of binding which is proportional to ln(Kd). Explicitly: deltaG=RTln(Kd) where R=ideal gas constant and T=temperature.

FIGS. 11A-B are graphs of oxopiperazine analog binding to His$_6$-tagged Mdm2 determined by a fluorescence-polarization assay (FIG. 11A) and to p300-CH1 determined by tryptophan fluorescence spectroscopy (FIG. 11B).

DETAILED DESCRIPTION OF THE INVENTION

Figure 1:
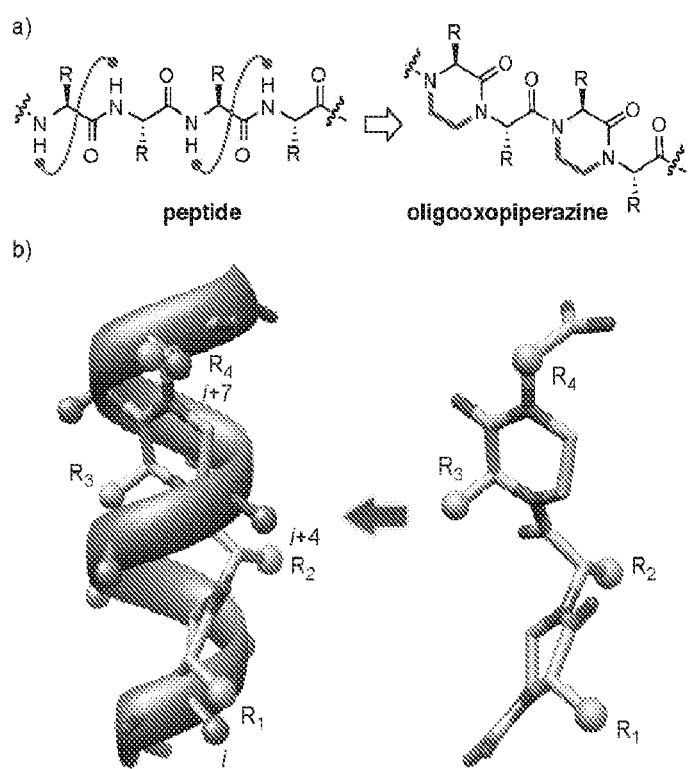
FIGS. 1A-B relate to the design of oxopiperazine helix mimetics.
Figure 2:
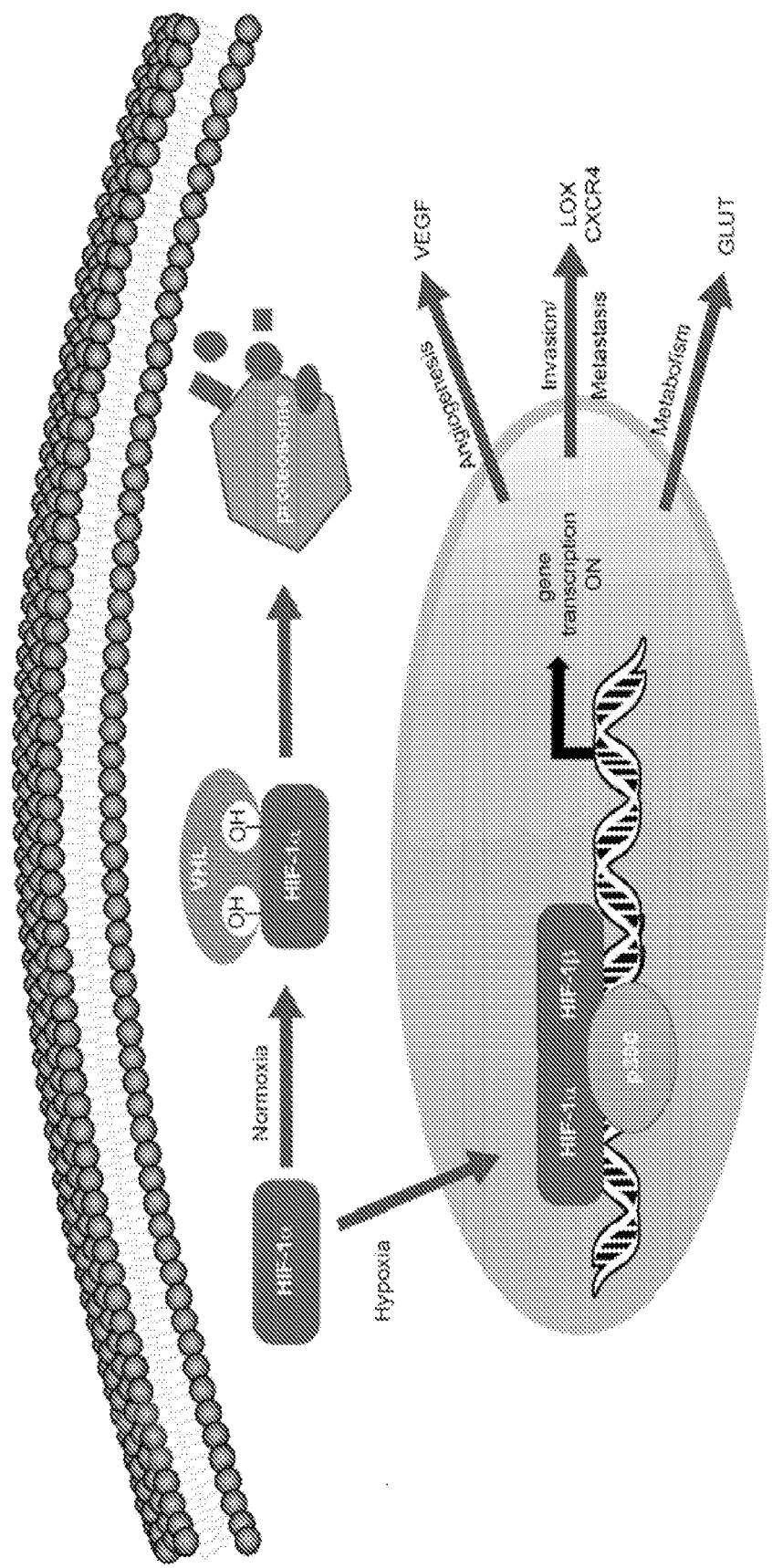
FIG. 2 is a schematic illustration of HIF1α-mediated regulation of oxygen-dependent transcription (Rankin & Giaccia, *Cell Death Different.* 15:678 (2008), which is hereby incorporated by reference in its entirety).
Figure 4:
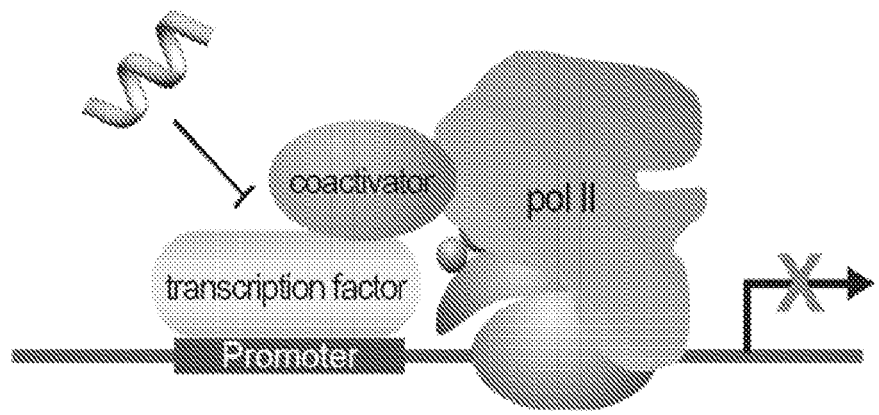
FIG. 4 is a schematic diagram illustrating the interaction between transcription factors, coactivators, and promoters in initiating transcription (Guarracino et al., *Biopolymers* 95:1 (2011), which is hereby incorporated by reference in its entirety).

As illustrated in FIG. 4, transcription factors are involved in an intricate web of interactions with partner proteins and promoter DNA, which result in recruitment of chromatin-remodeling enzymes and assembly of the preinitiation complex (MARK PTASHNE & ALEXANDER GANN, GENES AND SIGNALS (2002), which is hereby incorporated by reference in its entirety). Because of the essential role gene expression plays in the progression of diseases, synthetic agents that modulate transcription in a defined manner are attractive candidates for drug design (Arndt, *Angew Chem. Int'l Ed. Engl.* 45:4552-60 (2006); Berg, "*Curr. Opin. Chem. Biol.* 12:464-71 (2008); Mapp, *Org. Biomol. Chem.* 1:2217-20 (2003), each of which is hereby incorporated by reference in its entirety). Described herein is the design of oxopiperazine helix mimetics (OHMs) that inhibit transcription of hypoxia inducible genes by modulating the interaction between HIF1α transcription factor and coactivator p300/CBP. These oxopiperazines mimic helix αB of the C-terminal transactivation domain ("C-TAD") of HIF1α and include one or more side chains from a non-natural amino acid.

One aspect of the present invention relates to an oxopiperazine selected from the group consisting of
(i) Formula IA:

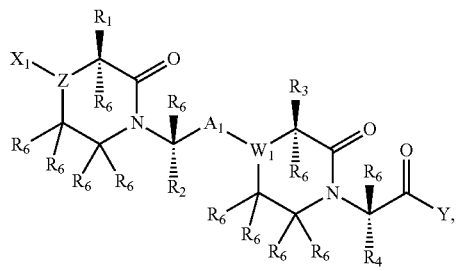

IA wherein:
$R_1$ is hydrophobic and is an amino acid side chain, OR, SR, an alkyl, or an aryl; wherein R is independently H, an alkyl, or an aryl;
$R_2$ is an amino acid side chain, OR, SR, an alkyl, or an aryl; wherein R is independently H, an alkyl, or an aryl; wherein $R_2$ is either a leucine side chain or longer than a leucine side chain by at least one backbone methylene; and with the proviso that $R_1$ and $R_2$ are not both an aryl;
$R_3$ is hydrophobic and is an amino acid side chain, SR, or an alkyl; wherein R is independently H, an alkyl, or an aryl;
$R_4$ is a hydrogen bond donor, a hydrophobic amino acid side chain, or an amide;
each $R_6$ is independently H, $N(R)_2$, OR, halogen, an alkyl, or an aryl; wherein each R is independently H, an alkyl, or an aryl;
$X_1$ is H, $N(R)_2$, OR, COR', $CO_2R'$, CONR', an alkyl, an aryl, an arylalkyl, a cycloalkyl, a heteroaryl, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;
Z is N, O, or S;
$A_1$-$W_1$ is:

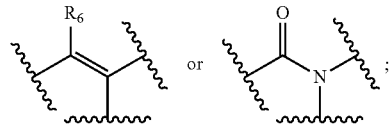

and
Y is OR', $N(R''')_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag;

(ii) Formula IB:

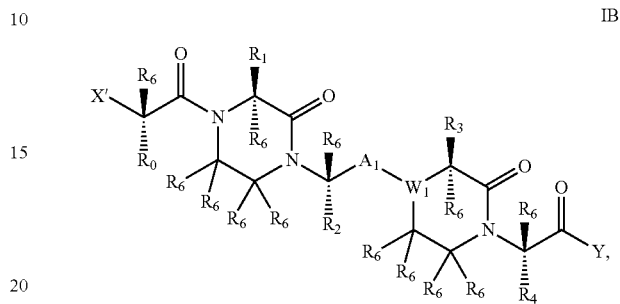

IB wherein:
$R_0$ is hydrophobic and is an amino acid side chain, OR, SR, an alkyl, or an aryl; wherein R is independently H, an alkyl, or an aryl;
$R_1$ and $R_2$ are each independently a solubilizing group, a hydrophobic amino acid side chain, H, $N(R)_2$, OR, SR, halogen, an alkyl, or an aryl; wherein each R is independently H, an alkyl, or an aryl;
$R_3$ is an amino acid side chain, OR, SR, an alkyl, or an aryl; wherein R is independently H, an alkyl, or an aryl; wherein $R_2$ is either a leucine side chain or longer than a leucine side chain by at least one backbone methylene; and with the proviso that $R_0$ and $R_3$ are not both an aryl;
$R_4$ is a hydrogen bond donor, a hydrophobic amino acid side chain, or an amide;
each $R_6$ is independently H, $N(R)_2$, OR, halogen, an alkyl, or an aryl; wherein each R is independently H, an alkyl, or an aryl;
X' is H, COR', $CO_2R'$, CONR', OR', $N(R'')_2$, an alkyl, an aryl, an arylalkyl, a cycloalkyl, a heteroaryl, a solubilizing group, a targeting moiety, or a tag; wherein R' is H, an alkyl, an aryl, an arylalkyl, a cycloalkyl, a heteroaryl, an amino acid residue, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a targeting moiety, or a tag; and wherein each R'' is independently H, $CO_2R'$, CONR', an alkyl, an aryl, an arylalkyl, a cycloalkyl, a heteroaryl, a targeting moiety, or a tag;
$A_1$-$W_1$ is:

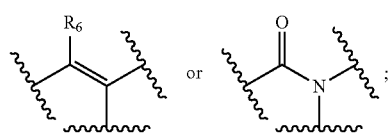

and
Y is OR', $N(R''')_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag;

and (iii) Formula IC:

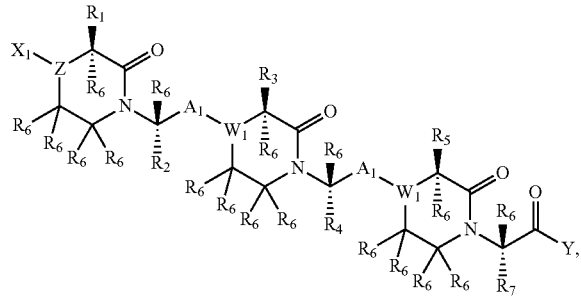

IC wherein:
$R_1$ is hydrophobic and is an amino acid side chain, OR, SR, an alkyl, or an aryl; wherein R is independently H, an alkyl, or an aryl;

$R_2$ is an amino acid side chain, OR, SR, an alkyl, or an aryl; wherein R is independently H, an alkyl, or an aryl; wherein $R_2$ is either a leucine side chain or longer than a leucine side chain by at least one backbone methylene; and with the proviso that $R_1$ and $R_2$ are not both an aryl;

$R_3$ is hydrophobic and is an amino acid side chain, SR, or an alkyl; wherein R is independently H, an alkyl, or an aryl;

$R_4$ is a hydrogen bond donor or an amide;

$R_5$ is a hydrophobic amino acid side chain;

each $R_6$ is independently H, $N(R)_2$, OR, halogen, an alkyl, or an aryl; wherein each R is independently H, an alkyl, or an aryl;

$R_7$ is a solubilizing group, a hydrophobic amino acid side chain, H, $N(R)_2$, OR, SR, halogen, an alkyl, or an aryl; wherein each R is independently H, an alkyl, or an aryl;

$X_1$ is H, $N(R)_2$, OR, COR', $CO_2R'$, CONR', an alkyl, an aryl, an arylalkyl, a cycloalkyl, a heteroaryl, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag; with the proviso that $X_1$ is absent when Z is O or S;

Z is N, O, or S;

each $A_1$-$W_1$ is independently:

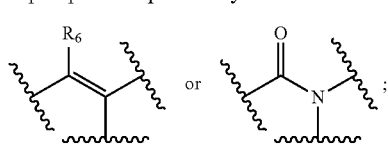

and
Y is OR', $N(R''')_2$, an alkyl, an aryl, an arylalkyl, a cycloalkyl, a heteroaryl, an amino acid, a peptide of 1 to 5 amino acid residues, a peptide of 1 to 6 amino acid residues, a peptide of 1 to 7 amino acid residues, a peptide of 1 to 8 amino acid residues, a peptide of 1 to 9 amino acid residues, a peptide of 1 to 10 amino acid residues, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag.

Amino acid side chains according to this and all aspects of the present invention can be any amino acid side chain—from natural or nonnatural amino acids—including alpha amino acids, disubstituted amino acids, beta amino acids, gamma amino acids, L-amino acids, D-amino acids, halogenated amino acids, etc. Hydrophobic amino acid side chains are well known in the art and include, for example, phenylalanine, tryptophan, leucine, alanine, isoleuceine, valine, tyrosine, norleucine, homoleucine, 3-chloro-phenylalanine, naphthaline, 3-methyl-phenylalanine, 4-chloro-phenylalanine, and (O—R)-tyrosine.

As used herein, the term "alkyl" means an aliphatic hydrocarbon group which may be straight or branched having about 1 to about 6 carbon atoms in the chain, unless otherwise specified. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

As used herein, the term "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

As used herein, the term "arylalkyl" refers to a radical of the formula —$R^aR^b$ where $R^a$ is an alkyl radical as defined above and $R^b$ is an aryl radical as defined above. The alkyl radical and the cycloalkyl radical may be optionally substituted as defined above.

As used herein, "heteroaryl" refers to an aromatic ring radical which consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCY- CLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

Solubilizing groups according to this and all aspects of the present invention include, without limitation, lysine, arginine, and poly(ethylene glycol).

The oxopiperazines of Formula IA, Formula IB, or Formula IC may comprise a protecting group that is suitable for the protection of an amine or a carboxylic acid. Such protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G. M. WUTS, PROTECTIVE GROUPS IN ORGANIC SYNTHESIS 494-615 (1999), which is hereby incorporated by reference in its entirety. Protecting groups that are suitable for the protection of a carboxylic acid are also well known in the art. Suitable carboxylic acid protecting groups include, without limitation, esters (e.g., substituted methyl esters, 2-substituted ethyl esters, 2,6-dialkylphenyl esters, substituted benzyl esters, silyl esters, and stannyl esters), amides, and hydrazides as described by THEODORA W. GREENE & PETER G. M. WUTS, PROTECTIVE GROUPS IN ORGANIC SYNTHESIS 372-450 (1999), which is hereby incorporated by reference in its entirety. Methods of protecting and deprotecting amine and carboxylic acids vary depending on the chosen protecting group; however, these methods are well known in the art and described in THEODORA W. GREENE & PETER G. M. WUTS, PROTECTIVE GROUPS IN ORGANIC SYNTHESIS 372-450 and 494-615 (1999), which is hereby incorporated by reference in its entirety.

A targeting moiety according to the present invention functions to (i) promote the cellular uptake of the oxopiperazine, (ii) target the oxopiperazine to a particular cell or tissue type (e.g., signaling peptide sequence), or (iii) target the oxopiperazine to a specific sub-cellular localization after cellular uptake (e.g., transport peptide sequence).

To promote the cellular uptake of an oxopiperazine of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., Org. Biomol. Chem. 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of the oxopiperazine is an "importation competent" signal peptide as disclosed by U.S. Pat. No. 6,043,339 to Lin et al., which is hereby incorporated by reference in its entirety. An importation competent signal peptides is generally about 10 to about 50 amino acid residues in length, typically hydrophobic residues, that render the oxopiperazine capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., Protein Seq. Data Anal. 1(1):41-42 (1987), which is hereby incorporated by reference in its entirety).

Another suitable targeting moiety is a signal peptide sequence capable of targeting the oxopiperazine to a particular tissue or cell type. The signaling peptide can include at least a portion of a ligand binding protein. Suitable ligand binding proteins include high-affinity antibody fragments (e.g., Fab, Fab' and F(ab')$_2$), single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified oxopiperazine is delivered intravenously or otherwise introduced into blood or lymph, the oxopiperazine will adsorb to the targeted cell, and the targeted cell will internalize the oxopiperazine. For example, if the target cell is a cancer cell, the oxopiperazine may be conjugated to an anti-C3B(I) antibody as disclosed by U.S. Pat. No. 6,572,856 to Taylor et al., which is hereby incorporated by reference in its entirety. Alternatively, the oxopiperazine may be conjugated to an alphafeto protein receptor as disclosed by U.S. Pat. No. 6,514,685 to Moro, or to a monoclonal GAH antibody as disclosed by U.S. Pat. No. 5,837,845 to Hosokawa, each of which is hereby incorporated by reference in its entirety. For targeting an oxopiperazine to a cardiac cell, the oxopiperazine may be conjugated to an antibody recognizing elastin microfibril interfacer (EMILIN2) (Van Hoof et al., J. Proteom. Res. 9:1610-18 (2010), which is hereby incorporated by reference in its entirety), cardiac troponin I, connexin-43, or any cardiac cell-surface membrane receptor that is known in the art. For targeting an oxopiperazine to a hepatic cell, the signaling peptide may include a ligand domain specific to the hepatocyte-specific asialoglycoprotein receptor. Such chimeric oxopiperazines can be prepared using similar methods as those for preparing chimeric proteins and peptides described in U.S. Pat. No. 5,817,789 to Heartlein et al., which is hereby incorporated by reference in its entirety.

Another suitable targeting moiety is a transport peptide that directs intracellular compartmentalization of the oxopiperazine once it is internalized by a target cell or tissue. For example, if the protein activity or protein-protein interaction that is sought to be inhibited occurs in the endoplasmic reticulum (ER), the oxopiperazine can be conjugated to an ER transport peptide sequence. A number of such signal peptides are known in the art, including the signal peptide MMSFVSLLLVGILFYATEAEQLTKCEVFQ (SEQ ID NO: 2). Other suitable ER signal peptides include the N-terminus endoplasmic reticulum targeting sequence of the enzyme 17β-hydroxysteroid dehydrogenase type 11 (Horiguchi et al., Arch. Biochem. Biophys. 479(2):121-30 (2008), which is hereby incorporated by reference in its entirety), or any of the ER signaling peptides (including the nucleic acid sequences encoding the ER signal peptides) disclosed in U.S. Patent Publication No. 20080250515 to Reed et al., which is hereby incorporated by reference in its entirety. Additionally, the oxopiperazine of the present invention can contain an ER retention signal, such as the retention signal KEDL (SEQ ID NO: 3). Methods of modifying the oxopiperazines of the present invention to incorporate transport peptides for localization of the oligomers to the ER can be carried out as described in U.S. Patent Publication No. 20080250515 to Reed et al., which is hereby incorporated by reference in its entirety.

If the protein activity or protein-protein interaction that is sought to be inhibited occurs in the nucleus, the oxopiperazine can include a nuclear localization transport signal. Suitable nuclear transport peptide sequences are known in the art, including the nuclear transport peptide PPKKKRKV (SEQ ID NO: 4). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the accordance with this aspect of the invention.

Suitable transport peptide sequences for targeting to the mitochondria include MLSLRQSIRFFKPATRTLCSSRYLL (SEQ ID NO: 5). Other suitable transport peptide sequences suitable for selectively targeting the oxopiperazine of the present invention to the mitochondria are disclosed in U.S. Published Patent Application No. 20070161544 to Wipf, which is hereby incorporated by reference in its entirety.

A "tag" as used herein includes any labeling moiety that facilitates the detection, quantitation, separation, and/or purification of the oxopiperazine of the present invention. Suitable tags include purification tags, radioactive or fluorescent labels, and enzymatic tags.

Purification tags, such as poly-histidine ($His_6$), a glutathione-S-transferase (GST-), or maltose-binding protein (MBP-), can assist in oligomer purification or separation but can later be removed, i.e., cleaved from the oxopiperazine following recovery. Protease-specific cleavage sites can be used to facilitate the removal of the purification tag. The desired oxopiperazine product can be purified further to remove the cleaved purification tags.

Other suitable tags include radioactive labels, such as, $^{125}I$, $^{131}I$, $^{111}In$, or $^{99}TC$. Methods of radiolabeling compounds, are known in the art and described in U.S. Pat. No. 5,830,431 to Srinivasan et al., which is hereby incorporated by reference in its entirety. Radioactivity is detected and quantified using a scintillation counter or autoradiography. Alternatively, the oxopiperazine can be conjugated to a fluorescent tag. Suitable fluorescent tags include, without limitation, chelates (europium chelates), fluorescein and its derivatives, rhodamine and its derivatives, dansyl, Lissamine, phycoerythrin and Texas Red. The fluorescent labels can be conjugated to the oxopiperazine using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., *Methods for the Preparation of Enzyme—Antibody Conjugates for Use in Enzyme Immunoassay*, in METHODS IN ENZYMOLOGY 147-66 (Langone et al. eds., 1981), which is hereby incorporated by reference in its entirety, can be used for conjugating enzymes to oxopiperazines of the present invention. Such tags may be particularly useful for detecting inhibition of protein-protein interactions using the oxopiperazine of the present invention.

The oxopiperazines of Formula IA, Formula IB, or Formula IC can also comprise a hydrogen bond donor. Hydrogen bond donors contain an electronegative atom with at least one proton to share. Suitable examples include, without limitation, amine, amide, carboxylic acids, hydroxyl, and thiol functional groups.

In one embodiment of the present invention, the oxopiperazine has a formula of Formula IA. In a preferred embodiment, $R_1$ is OR, SR, a $C_3$-$C_6$ alkyl, an aryl, or a side chain of an amino acid selected from the group consisting of leucine, methionine, and homoleucine. In a preferred embodiment, $R_2$ is OR, SR, a $C_3$-$C_6$ alkyl, an aryl, or a side chain of an amino acid selected from the group consisting of norleucine, methionine, leucine, and homoleucine. In a preferred embodiment, $R_3$ is SR, a $C_1$-$C_3$ alkyl, or a side chain of an amino acid selected from the group consisting of glycine and alanine. In a preferred embodiment, $R_4$ is a side chain of an amino acid selected from the group consisting of glutamine, alanine, valine, asparagine, serine, and homoserine. In a preferred embodiment, Y is OH, OR', NHR', NR'$_2$, or NH$_2$. Combinations of these embodiments are also contemplated. In further preferred embodiments, $R_1$, $R_2$, $R_3$, and $R_4$ are amino acid side chains as shown in Table 1 below. Combinations of these embodiments are also contemplated.

TABLE 1

Exemplary Embodiments of Formula IA

| Emb. | $R_1$ | $R_2$ | $R_3$ | $R_4$ |
|---|---|---|---|---|
| A | Leu | Nle | Ala | Gln |
| B | Met | Met | Ala | Gln |
| C | Hle | Hle | Ala | Gln |
| D | Hle | Leu | Ala | Gln |
| E | Met | Leu | Ala | Gln |
| F | Leu | Hle | Ala | Gln |
| G | Hle | Nle | Ala | Gln |

In one embodiment of the present invention, the oxopiperazine has a formula of Formula IB. In a preferred embodiment, $R_0$ is OR, SR, a $C_3$-$C_6$ alkyl, an aryl, or a side chain of an amino acid selected from the group consisting of leucine, methionine, and homoleucine. In a preferred embodiment, $R_3$ is OR, SR, a $C_3$-$C_6$ alkyl, an aryl, or a side chain of an amino acid selected from the group consisting of norleucine, methionine, leucine, and homoleucine. In a preferred embodiment, $R_4$ is a side chain of an amino acid selected from the group consisting of glutamine, alanine, valine, asparagine, serine, and homoserine. In a preferred embodiment, Y is OH, OR', NHR', NR'$_2$, or NH$_2$. Combinations of these embodiments are also contemplated. In further preferred embodiments, $R_0$, $R_3$, and $R_4$ are amino acid side chains as shown in Table 2 below.

TABLE 2

Exemplary Embodiments of Formula IB

| Emb. | $R_0$ | $R_3$ | $R_4$ |
|---|---|---|---|
| A | Leu | Nle | Gln |
| B | Met | Met | Gln |
| C | Hle | Hle | Gln |
| D | Hle | Leu | Gln |
| E | Met | Leu | Gln |
| F | Leu | Hle | Gln |
| G | Hle | Nle | Gln |

In one embodiment of the present invention, the oxopiperazine has a formula of Formula IC. In a preferred embodiment, $R_1$ is OR, SR, a $C_3$-$C_6$ alkyl, an aryl, or a side chain of an amino acid selected from the group consisting of leucine, methionine, and homoleucine. In a preferred embodiment, $R_2$ is OR, SR, a $C_3$-$C_6$ alkyl, an aryl, or a side chain of an amino acid selected from the group consisting of norleucine, methionine, leucine, and homoleucine. In a preferred embodiment, $R_4$ is a side chain of an amino acid selected from the group consisting of glutamine, asparagine, and homoserine. In a preferred embodiment, $R_5$ is a side chain of an amino acid selected from the group consisting of alanine, valine, and serine. In a preferred embodiment, Y is OH, OR', NHR', NR'$_2$, or NH$_2$. Combinations of these embodiments are also contemplated. In further preferred embodiments, $R_1$, $R_2$, $R_4$, and $R_5$ are amino acid side chains as shown in Table 3 below.

TABLE 3

Exemplary Embodiments of Formula IC

| Emb. | $R_1$ | $R_2$ | $R_4$ | $R_5$ |
|---|---|---|---|---|
| A | Leu | Nle | Gln | Val, Ala, or Leu |
| B | Met | Met | Gln | Val, Ala, or Leu |
| C | Hle | Hle | Gln | Val, Ala, or Leu |
| D | Hle | Leu | Gln | Val, Ala, or Leu |
| E | Met | Leu | Gln | Val, Ala, or Leu |
| F | Leu | Hle | Gln | Val, Ala, or Leu |
| G | Hle | Nle | Gln | Val, Ala, or Leu |

Exemplary oxopiperazine compounds of the present invention include, without limitation, OHMs 23-25 and 28-31. In a preferred embodiment, the oxopiperazine is has a Rosetta score below 7 R.E.U. In a preferred embodiment, the oxopoperizine is selected from the group consisting of OHM 23, OHM 25, OHM 30, and OHM 31.

Oxopiperazines of the present invention may be made using methods in the art. Suitable methods include those described in U.S. patent application Ser. No. 12/917,176, which is hereby incorporated by reference in its entirety.

Also encompassed by the present invention is a pharmaceutical formulation that includes an oxopiperazine of the present invention and a pharmaceutically acceptable vehicle.

Suitable pharmaceutical formulations include the oxopiperazine and any pharmaceutically acceptable adjuvants, carriers, solutions, suspensions, emulsions, excipients, powders, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of the oxopiperazine together with the adjuvants, carriers and/or excipients. The amount of active compound in such therapeutically useful compositions is such that a suitable dosage unit will be obtained.

In addition, the pharmaceutical formulations of the present invention may further comprise one or more pharmaceutically acceptable diluents or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

For oral therapeutic administration, the oxopiperazines of the invention may be incorporated with excipients and used in the form of tablets, capsules, elixirs, suspensions, syrups, and the like. Such compositions and preparations should contain at least 0.1% of the oxopiperazine. The percentage of the oxopiperazine in these compositions may, of course, be varied and may conveniently be between about 2% to about 60% of the weight of the unit. The amount of the oxopiperazine in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

Solutions or suspensions of the oxopiperazine (for example, for parenteral administration) can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

Pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Another aspect of the present invention relates to inhibiting the HIF1α-p300/CBP interaction using the oxopiperazines of the present invention.

One embodiment of this aspect of the present invention relates to a method of reducing transcription of a gene in a cell, where transcription of the gene is mediated by interaction of HIF1α with CREB-binding protein and/or p300. This method involves contacting the cell with an oxopiperazine of the present invention under conditions effective to cause nuclear uptake of the oxopiperazine, where the oxopiperazine disrupts interaction of HIF1α and p300/CBP and thereby reduces transcription of the gene.

Genes whose transcription is mediated by interaction of HIF1α with CBP and/or p300 include $α_{1B}$-adrenergic receptor, adenylate kinase 3, adrenomedullin, aldolase A, aldolase C, carbonic anhydrase IX, ceruloplasmin, chemokine receptor type 4 (CXCR4, fusin, CD184), c-Met, endothelin-1, enolase 1, erythropoietin, glucose transporter 1, glucose transporter 3, glyceraldehyde-3-phosphate dehydrogenase, heme oxygenase 1, hexokinase 1, hexokinase 2, IGF binding protein 1, IGF binding protein 3, insulin-like growth factor 2, lactate dehydrogenase A, lysyl oxidase, monoamine oxidase isoform A, monoamine oxidase isoform B, nitric oxide synthase 2, p21, p35$^{srg}$, phosphofructokinase, phosphoglycerate kinase 1, plasminogen activator inhibitor 1, pyruvate kinase M, stromal-derived factor 1, tranferrin receptor, transferrin, transforming growth factor $β_3$, triose phosphate isomerase 1, vascular endothelial growth factor, vascular endothelial growth factor receptor FLT-1, and vascular endothelial growth factor receptor KDR/Flk-1. Some uses for inhibiting transcription of these genes are shown in Table 4.

TABLE 4

Example Disorders

| Gene | Treat/prevent |
| --- | --- |
| adrenomedullin | Pheochromocytoma |
| carbonic anhydrase IX | Cancer |
| ceruloplasmin | Lymphoma, acute and chronic inflammation, rheumatoid arthritis |
| chemokine receptor type 4 (CXCR4, fusin, CD184) | Cancer stem cell migration, inflammation |
| c-Met | Metastasis (tumor, incl. cancer) |
| endothelin-1 | Abnormal vasoconstriction |
| enolase 1 | Hashimoto's encephalopathy, severe asthma |
| erythropoietin | Abnormal oxygen transport |
| glucose transporter 1 | Aerobic glycolysis (Warburg effect) |
| glucose transporter 3 | Aerobic glycolysis (Warburg effect) |
| heme oxygenase 1 | Abnormal oxygen transport |
| hexokinase 1 | Aerobic glycolysis (Warburg effect) |
| hexokinase 2 | Aerobic glycolysis (Warburg effect) |

TABLE 4-continued

Example Disorders

| Gene | Treat/prevent |
| --- | --- |
| IGF binding protein 1 | Abnormal development and function of organs (brain, liver) |
| IGF binding protein 3 | Abnormal development and function of organs (brain, liver) |
| insulin-like growth factor 2 | Abnormal development and function of organs (brain, liver) |
| lactate dehydrogenase A | Myocardial infarction |
| lysyl oxidase | Metastasis (tumor, esp. breast cancer) |
| monoamine oxidase isoform A | Aggression, depression, cancer, esp. prostate |
| monoamine oxidase isoform B | Aggression, depression, cancer, esp. prostate |
| nitric oxide synthase 2 | Abnormal vasomotor tone |
| phosphofructokinase | Aerobic glycolysis (Warburg effect) |
| phosphoglycerate kinase 1 | Aerobic glycolysis (Warburg effect) |
| stromal-derived factor 1 | Cancer stem cell migration, inflammation |
| tranferrin receptor | Abnormal iron uptake/metabolism |
| transferrin | Abnormal iron uptake/metabolism |
| triose phosphate isomerase 1 | Aerobic glycolysis (Warburg effect) |
| vascular endothelial growth factor | Angiogenesis (tumor, incl. cancer) |
| vascular endothelial growth factor receptor FLT-1 | Angiogenesis (tumor, incl. cancer) |
| vascular endothelial growth factor receptor KDR/Flk-1 | Angiogenesis (tumor, incl. cancer) |

Another embodiment of this aspect of the present invention relates to a method of treating or preventing in a subject a disorder mediated by interaction of HIF1α with CBP and/or p300. This method involves administering an oxopiperazine of the present invention to the subject under conditions effective to treat or prevent the disorder.

The present invention provides for both prophylactic and therapeutic methods of treating a subject at risk of (or susceptible to) a disorder or having a disorder mediated by interaction of HIF1α with CBP and/or p300. This is because the oxopiperazines are expected to act as inhibitors of HIF1α binding to CBP and/or p300. As used herein, the term "treatment" is defined as the application or administration of a therapeutic agent to a patient, or application or administration of a therapeutic agent to an isolated tissue or cell line from a patient, who has a disease, a symptom of disease, or a predisposition toward a disease, with the purpose to cure, heal, alleviate, relieve, alter, remedy, ameliorate, improve, or affect the disease, the symptoms of disease, or the predisposition toward disease.

Disorders that can be treated or prevented include, for example, retinal ischemia (Zhu et al., *Invest. Ophthalmol. Vis. Sci.* 48:1735-43 (2007); Ding et al., *Invest. Ophthalmol. Vis. Sci.* 46:1010-6 (2005), each of which is hereby incorporated by reference in its entirety), pulmonary hypertension (Simon et al., *Annu. Rev. Physiol.* 70:51-71 (2008); Eul et al., *FASEB J.* 20:163-5 (2006), each of which is hereby incorporated by reference in its entirety), intrauterine growth retardation (Caramelo et al., *Medicina B. Aires* 66:155-64 (2006); Tazuke et al., *Proc. Nat'l Acad. Sci. USA* 95:10188-93 (1998), each of which is hereby incorporated by reference in its entirety), diabetic retinopathy (Ritter et al., *J. Clin. Invest.* 116:3266-76 (2006); Wilkinson-Berka et al., *Curr. Med. Chem.* 13:3307-17 (2006); Vinores et al., *J. Cell. Physiol.* 206:749-58 (2006); Caldwell et al., *Curr. Drug Targets* 6:511-24 (2005), each of which is hereby incorporated by reference in its entirety), age-related macular degeneration (Inoue et al., *Br. J. Ophthalmol.* 91:1720-1 (2007); Zuluaga et al., *Invest. Ophthalmol. Vis. Sci.* 48:1767-

72 (2007); Provis, Prog. *Retin. Eye Res.* 20:799-821 (2001), each of which is hereby incorporated by reference in its entirety), diabetic macular edema (Vinores et al., *J. Cell. Physiol.* 206:749-58 (2006); Forooghian & Das, *Am. J. Ophthalmol.* 144:761-8 (2007), each of which is hereby incorporated by reference in its entirety), and cancer (Marignol et al., *Cancer Treat. Rev.* 34:313-27 (2008); Galanis et al., *Cancer Lett.* 266:12-20 (2008); Ushio-Fukai & Nakamura, *Cancer Lett.* 266:37-52 (2008); Adamski et al., *Cancer Treat. Rev.* 34:231-46 (2008); Toffoli & Michiels, *FEBS J.* 275:2991-3002 (2008); Peehl & Coram, *J. Urol.* 180: 2206-11 (2008); Flamand & Zhao, *J. Cancer Res. Clin. Oncol.* 136:1761-71 (2010), each of which is hereby incorporated by reference in its entirety).

The subject according to this aspect of the present invention can be, for example, any vertebrate, e.g., mammals, fish, reptiles, birds, and amphibians. Suitable mammals include, for example, primates, felines, canines, rodents (e.g., mice and rats), and livestock (e.g., cattle, sheep, pigs, goats, and horses). In a preferred embodiment, the subject is a human subject.

Yet another embodiment of this aspect of the present invention relates to a method of reducing or preventing angiogenesis in a tissue. This method involves contacting the tissue with an oxopiperazine of the present invention under conditions effective to reduce or prevent angiogenesis in the tissue.

Another embodiment of this aspect of the present invention relates to a method of inducing apoptosis of a cell. This method involves contacting the cell with an oxopiperazine of the present invention under conditions effective to induce apoptosis of the cell.

Another embodiment of this aspect of the present invention relates to a method of decreasing survival and/or proliferation of a cell. This method involves contacting the cell with an oxopiperazine of the present invention under conditions effective to decrease survival and/or proliferation of the cell.

Suitable cells according to the methods of the present invention include, without limitation, any vertebrate cell, e.g., mammalian, ichthian, reptilian, avian, and amphibian cells. Suitable mammalian cells include, for example, those of primates, felines, canines, rodents (e.g., mice and rats), and livestock (e.g., cattle, sheep, pigs, goats, and horses). In a preferred embodiment, the cells are human cells.

Contacting (including administering) according to the methods of the present invention can be carried out using methods that will be apparent to the skilled artisan, and can be done in vitro or in vivo.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

This liposome delivery system can also be made to accumulate at a target organ, tissue, or cell via active targeting (e.g., by incorporating an antibody or hormone on the surface of the liposomal vehicle). This can be achieved according to known methods.

An alternative approach for delivery of protein- or polypeptide-containing agents (e.g., oxopiperazines of the present invention containing one or more protein or polypeptide side chains) involves the conjugation of the desired agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of agents involves preparation of chimeric agents according to U.S. Pat. No. 5,817,789 to Heartlein et al., which is hereby incorporated by reference in its entirety. The chimeric agent can include a ligand domain and the agent (e.g., an oxopiperazine of the invention). The ligand domain is specific for receptors located on a target cell. Thus, when the chimeric agent is delivered intravenously or otherwise introduced into blood or lymph, the chimeric agent will adsorb to the targeted cell, and the targeted cell will internalize the chimeric agent.

Oxopiperazines of the present invention may be delivered directly to the targeted cell/tissue/organ.

Additionally and/or alternatively, the oxopiperazines may be administered to a non-targeted area along with one or more agents that facilitate migration of the oxopiperazines to (and/or uptake by) a targeted tissue, organ, or cell. As will be apparent to one of ordinary skill in the art, the oxopiperazine itself can be modified to facilitate its transport to a target tissue, organ, or cell, including its transport across the blood-brain barrier; and/or to facilitate its uptake by a target cell (e.g., its transport across cell membranes). In a preferred embodiment, the oxopiperazine of the invention is modified, and/or delivered with an appropriate vehicle, to facilitate its delivery to the nucleus of the target cell (Wender et al., *Proc. Nat'l Acad. Sci. USA* 97:13003-8 (2000); Roberts, *Scientist* 18:42-3 (2004); Joliot & Prochiantz, *Nat. Cell Biol.* 6:189-96 (2004), each of which is hereby incorporated by reference in its entirety). Some example target cells, tissues, and/or organs for the embodiments described above are shown in Table 5.

TABLE 5

Example Target Cells/Tissues/Organs

| Desired Effect | Example Target(s) |
|---|---|
| Inhibit transcription of: | |
| adrenomedullin | Pheochromocytoma |
| carbonic anhydrase IX | Tumor cells/tissue, incl. cancer |
| ceruloplasmin | Lymphocytes/lymphatic tissue, inflamed tissue, rheumatoid arthritic tissue |
| chemokine receptor type 4 (CXCR4, fusin, CD184) | Tumor cells/tissue, incl. cancer |
| c-Met | Tumor cells/tissue, incl. cancer |
| endothelin-1 | Endothelium |
| enolase 1 | Liver, brain, kidney, spleen, adipose, lung |
| erythropoietin | Liver, kidney |
| glucose transporter 1 | Tumor, incl. cancer |
| glucose transporter 3 | Tumor, incl. cancer |
| hexokinase 1 | Tumor, incl. cancer |
| hexokinase 2 | Tumor, incl. cancer |
| IGF binding protein 1 | Brain, liver |
| IGF binding protein 3 | Brain, liver |
| insulin-like growth factor 2 | Brain, liver |
| lactate dehydrogenase A | Heart |
| lysyl oxidase | Tumor cells/tissue, incl. cancer |
| monoamine oxidase isoform A | Tumor cells/tissue, esp. prostate cancer |
| monoamine oxidase isoform B | Tumor cells/tissue, esp. prostate cancer |
| nitric oxide synthase 2 | Vessels, cardiovascular cells/tissue |
| phosphofructokinase | Tumor, incl. cancer |
| phosphoglycerate kinase 1 | Tumor, incl. cancer |
| stromal-derived factor 1 | Tumor cells/tissue, incl. cancer |
| transferrin | Liver |
| triose phosphate isomerase 1 | Tumor, incl. cancer |
| vascular endothelial growth factor (VEGF) | Tumor cells/tissue, incl. cancer |

TABLE 5-continued

Example Target Cells/Tissues/Organs

| Desired Effect | Example Target(s) |
| --- | --- |
| VEGF receptor FLT-1 | Tumor cells/tissue, incl. cancer |
| VEGF receptor KDR/Flk-1 | Tumor cells/tissue, incl. cancer |
| Treat or prevent: | |
| retinal ischemia | Retina (eye) |
| pulmonary hypertension | Lungs |
| intrauterine growth retardation | Uterus |
| diabetic retinopathy | Retina (eye) |
| age-related macular degeneration | Retina (eye) |
| diabetic macular edema | Retina (eye) |
| Reduce or prevent angiogenesis | Tumor cells/tissue, incl. cancer |
| Reduce or prevent metastasis | Tumor cells/tissue, incl. cancer |
| Decrease cell survival and/or proliferation | Cancerous cells, cells contained in the endothelial vasculature of a tissue that contains cancerous cells |

In vivo administration can be accomplished either via systemic administration to the subject or via targeted administration to affected tissues, organs, and/or cells, as described above. Typically, the therapeutic agent (i.e., an oxopiperazine of the present invention) will be administered to a patient in a vehicle that delivers the therapeutic agent(s) to the target cell, tissue, or organ. Typically, the therapeutic agent will be administered as a pharmaceutical formulation, such as those described above.

Exemplary routes of administration include, without limitation, orally, topically, transdermally, parenterally, subcutaneously, intravenously, intramuscularly, intraperitoneally, intraventricularly, and intralesionally; by intratracheal inoculation, aspiration, airway instillation, aerosolization, nebulization, intranasal instillation, oral or nasogastric instillation, intraperitoneal injection, intravascular injection, intravenous injection, intra-arterial injection (such as via the pulmonary artery), intramuscular injection, and intrapleural instillation; by application to mucous membranes (such as that of the nose, throat, bronchial tubes, genitals, and/or anus); and by implantation of a sustained release vehicle.

For use as aerosols, an oxopiperazine of the present invention in solution or suspension may be packaged in a pressurized aerosol container together with suitable propellants, for example, hydrocarbon propellants like propane, butane, or isobutane with conventional adjuvants. The oxopiperazines of the present invention also may be administered in a non-pressurized form.

Exemplary delivery devices include, without limitation, nebulizers, atomizers, liposomes (including both active and passive drug delivery techniques) (Wang & Huang, *Proc. Nat'l Acad. Sci. USA* 84:7851-5 (1987); Bangham et al., *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al.; Wolff et al., *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the oxopiperazine to the desired organ, tissue, or cells in vivo to effect this aspect of the present invention.

Contacting (including in vivo administration) can be carried out as frequently as required and for a duration that is suitable to provide the desired effect. For example, contacting can be carried out once or multiple times, and in vivo administration can be carried out with a single sustained-release dosage formulation or with multiple (e.g., daily) doses.

The amount to be administered will, of course, vary depending upon the particular conditions and treatment regimen. The amount/dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the oxopiperazine of the invention are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

The present invention may be further illustrated by reference to the following examples.

EXAMPLES

The following Examples are intended to illustrate, but by no means are intended to limit, the scope of the present invention as set forth in the appended claims.

Example 1—General Materials and Methods

Commercial-grade reagents and solvents were used without further purification except as indicated. All reactions were stirred magnetically or mechanically shaken; moisture-sensitive reactions were performed under nitrogen atmosphere. Reverse-phase HPLC experiments were conducted with 0.1% aqueous trifluoroacetic acid and 0.1% trifluoroacetic acid in acetonitrile buffers as eluents on $C_{18}$ reversed-phase columns using a Beckman Coulter HPLC equipped with a System Gold 168 Diode array detector. ESIMS data was obtained on an Agilent 1100 series LC/MSD (XCT) electrospray trap. The microwave reactions were performed in the CEM Discover single-mode reactor with controlled power, temperature, and time settings. The NMR spectra of oxopiperazine compounds were recorded on a Bruker AVANCE 400, 500, or 600 MHz spectrometer.

Example 2—p300-CH1 Plasmids

The DNA sequence of the human p300 CH1 domain (amino acid residues 323-423) was subcloned into a pUC57 plasmid by Genscript, Inc. After transformation of JM109 bacteria (Promega) with the plasmid, it was amplified and purified. Then the gene of interest was subcloned between BamHI and EcoRI restriction sites of pGEX-4T-2 expression vector (Amersham).

Example 3—p300-CH1 Protein Expression and Purification

The pGEX-4T-2-p300 fusion vector was transformed into BL21(DE3) competent *E.coli* (Novagen) in M9 minimal media with $^{15}NH_4Cl$ as the primary nitrogen source. Protein production was induced with 1 mM IPTG at $OD_{600}$ of 1 for 16 hours at 15° C. Production of the desired p300-CH1-GST fusion product was verified by SDS-PAGE. Bacteria were harvested and resuspended in the lysis buffer with 20 mM Phosphate buffer (Research Products International, Corp.), 100 µM DTT (Fisher), 100 µM ZnSO$_4$ (Sigma), 0.5% TritonX 100 (Sigma), 1 mg/mL Pepstatin A (Research Products International, Corp.), 10 mg/mL Leupeptin A (Research Products International, Corp.), 500 µM PMSF (Sigma), and 0.5% glycerol at pH 8.0. Pellets were lysed by sonication and centrifuged at 4° C. and 20,000 rpm for 20 minutes. Fusion protein was collected from the bacterial supernatant and purified by affinity chromatography using glutathione Sepharose 4B beads (Amersham) prepared according to the manufacturer's directions. GST-tag was cleaved by thrombin and protein was eluted from resin. Collected fractions were assayed by SDS-PAGE gel; pooled fractions were treated with protease inhibitor cocktail (Sigma) and against a buffer containing 10 mM Tris, 50 mM NaCl, 2 mM DTT (Fisher), and 3 equivalents ZnSO$_4$ at pH 8.0 to ensure proper folding (vide supra).

Example 4—Docking and Design Protocol in Rosetta

The oxopiperazine dimer scaffold was initially docked by aligning Cβ atoms on the scaffold positions corresponding to hotspot residues on HIF1α (R$_1$: Leu818, R$_2$: Leu822, R$_4$: Gln824) using the PDB structure: 1L8C. The Rosetta relax w/constraints application was run on this initial structure to relieve any clashes that may hinder score analysis. The relaxed complex was then modeled and designed using a protocol developed specifically for oxopiperazine inhibitors. The protocol iterates between 1) a perturbation phase (conformational optimization), attempting to find the lowest energy conformation of bound ligand and target protein given the current residue identities; and 2) a design phase, which attempts to find residue substitutions including non-canonical analogues that lower the energy given the current conformation. The perturbation phase consists of a) rigid body rotation and translation moves, b) small angle moves of phi and psi, and c) pucker moves of the oxopiperazine rings. Perturbations were only allowed to the scaffold, leaving the target's backbone fixed. All residues at the interface on both target and ligand were allowed to sample side-chain rotamer space. The design phase consisted of residue identity substitutions at positions along the scaffold and rotamer repacking. Substitutions were defined in the Rosetta resfile. Finally, minimization of all degrees of freedom in the complex was performed.

For modeling analysis, the same design protocol was used, except residues were fixed to the identities of interest in the Rosetta residue input file (i.e., resfile). Fixing residue identities only allows side chain optimization during the "design" phase. 5000 independent runs (i.e., decoys) were computed for each sequence. For design runs, R$_1$ and R$_2$ were substituted with all hydrophobic noncanonical amino acids in Table 6 below except for proline analogs.

TABLE 6

Noncanonical Amino Acid Design Library for Rosetta (p300 Target) Positions R$_1$ and R$_2$
Rosetta code: noncanonical amino acid name NC A04: 1-amino-cyclopentane-carboxylic_acid_puck1
NC A05: 1-amino-cyclopentane-carboxylic_acid_puck2
NC A12: 2,4-dimethyl-phenylalanine
NC A20: 2-allyl-glycine
NC A24: 2-amino-2-phenylbutyric_acid TABLE 6-continued Noncanonical Amino Acid Design Library for Rosetta (p300 Target) Positions R$_1$ and R$_2$
Rosetta code: noncanonical amino acid name NC A30: 2-amino-4-bromo-4-pentenoic_acid
NC A31: 2-amino-5-phenyl-pentanoic_acid
NC A33: 2-amino-heptanoic_acid
NC A34: 2-aminomethyl-phenylalanine
NC A44: 2-indanyl-glycine_puck1
NC A45: 2-indanyl-glycine_puck2
NC A48: 2-methyl-phenylalanine
NC A84: 3-methyl-phenylalanine
NC A91: 4,5-dehydro-leucine
NC B04: 4-amino-tetrahydrothiopyran-4-carboxylic_acid_boat1
NC B05: 4-amino-tetrahydrothiopyran-4-carboxylic_acid_boat2
NC B06: 4-amino-tetrahydrothiopyran-4-carboxylic_acid_chair1
NC B07: 4-amino-tetrahydrothiopyran-4-carboxylic_acid_chair2
NC C90: 4-fluoro-tryptophan
NC B27: 4-methyl-phenylalanine
NC B28: 4-methyl-tryptophan
NC B30: 4-phenyl-phenylalanine
NC B31: 4-tert-butyl-phenylalanine
NC C80: 5-bromo-tryptophan
NC C81: 5-chloro-tryptophan
NC B35: 5-fluoro-tryptophan
NC B38: 5-methyl-tryptophan
NC C83: 6-bromo-tryptophan
NC C84: 6-chloro-tryptophan
NC C85: 6-fluoro-tryptophan
NC B40: 6-methyl-tryptophan
NC C86: 7-azatryptophan
NC C87: 7-bromo-tryptophan
NC C88: 7-methyl-tryptophan
NC B44: 9-anthryl-alanine
NC ABA: aminobutyric acid
NC B47: allo-isoleucine
NC B57: alpha-methyl-leucine
NC B58: alpha-methyl-phenylalanine
NC B60: alpha-methyl-tryptophan
NC B62: alpha-methyl-valine
NC B67: beta-(1-naphthyl)-alanine
NC B74: beta-(2-naphthyl)-alanine
NC B92: beta-beta-dicyclohexyl-alanine_boat_boat
NC B93: beta-beta-dicyclohexyl-alanine_boat_chair
NC B94: beta-beta-dicyclohexyl-alanine_chair_boat
NC B95: beta-beta-dicyclohexyl-alanine_chair_chair
NC B96: beta.beta-diphenyl-alanine
NC B97: beta-chloro-alanine
NC B99: beta-cyclohexyl-alanine_boat
NC C00: beta-cyclohexyl-alanine_chair
NC C01: beta-cyclopentyl-alanine
NC C02: beta-cyclopentyl-alanine_puck
NC C03: beta-fluoro-alanine
NC C05: beta-iodo-alanine
NC C11: cyclohexyl-glycine_boat
NC C12: cyclohexyl-glycine_chair
NC C15: diphenylglycine
NC C16: dipropyl-glycine
NC C20: ethionine
NC C91: fluoro-leucine_ent1
NC C92: fluoro-leucine_ent2
NC C93: hexafluoro-leucine
NC HLU: homoleucine
NC C26: homocysteine
NC C27: homophenylalanine
NC MAL: MAL
NC C12: MPA
NC C36: n-in-methyl-tryptophan
NC NLU: norleucine
NC NVL: norvaline
NC C41: penicillamine
NC C42: phenylglycine
NC C53: tert-butyl-alanine
NC C54: tert-butyl-cysteine
NC C55: tert-butyl-glycine
NC C60: trifluoro-alanine
NC C61: trifluoro-leucine
NC C94: trifluoro-leucine_ent2

Detailed protocols including command lines have been previously described (Drew et al., *PLoS One* 8:DOI: 10.1371/journal.pone.0067051 (2013), which is hereby incorporated by reference in its entirety).

Top designs were selected based on filtering the lowest 5% of total energy decoys and sorting by Rosetta binding energy score. The Rosetta binding energy score was calculated using equation (1).

$$\text{Binding\_energy\_score} = \text{total\_score} - \text{unbound\_score} \quad (1)$$

The unbound score was calculated by separating the scaffold from the target HIF1α structure, then repacking the side chains and finally calculating the total Rosetta energy of the unbound complex.

Example 5—Rosetta Binding Discrimination Analysis

A random set of designs against target protein p300 were generated from a set of 30,000 Rosetta design runs where all four positions of an oxopiperazine dimer were allowed to vary to any canonical amino acid excluding Cys, Gly, and Pro. The top 1000 of models by total Rosetta score made up the total random set. This random set is shown as a grey histogram (violin plot) in FIG. 5.

The top binding energy score for designs with experimental binding affinities were determined from a set of 5,000 decoy structures. As described above, the top 1000 of decoys by total score was then sorted by Rosetta binding energy score and the lowest Rosetta binding energy score was used.

Example 6—Quantum Mechanics Calculations

Quantum mechanics calculations were done using the Gaussian 09 (EM64L-G09RevC.01, version date: 2011-09-23) software package (Gaussian 09, Revision C.01, Frisch et al. (Gaussian, Inc. 2009), which is hereby incorporated by reference in its entirety). An initial optimization using "HF 6-31G(d) Opt SCRF=PCM SCF=Tight" parameters was done for each model structure. The resulting optimized structure was then used for further energy calculations with parameters "B3LYP 6-31G(d) Geom=Check SCRF=PCM SCF=Tight" and "MP2(full) 6-31G(d) Geom=Check SCRF=PCM SCF=Tight".

Example 7—Synthesis and Characterization of Oxopiperazines

The oxopiperazines were synthesized via solid phase synthesis as described in U.S. patent application Ser. No. 12/917,176 to Arora et al., which is hereby incorporated by reference in its entirety, as shown in Scheme 1 below.

Scheme 1

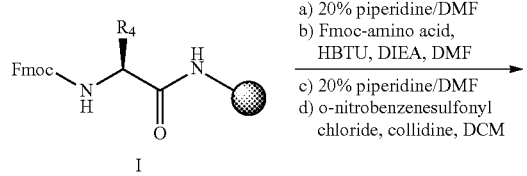
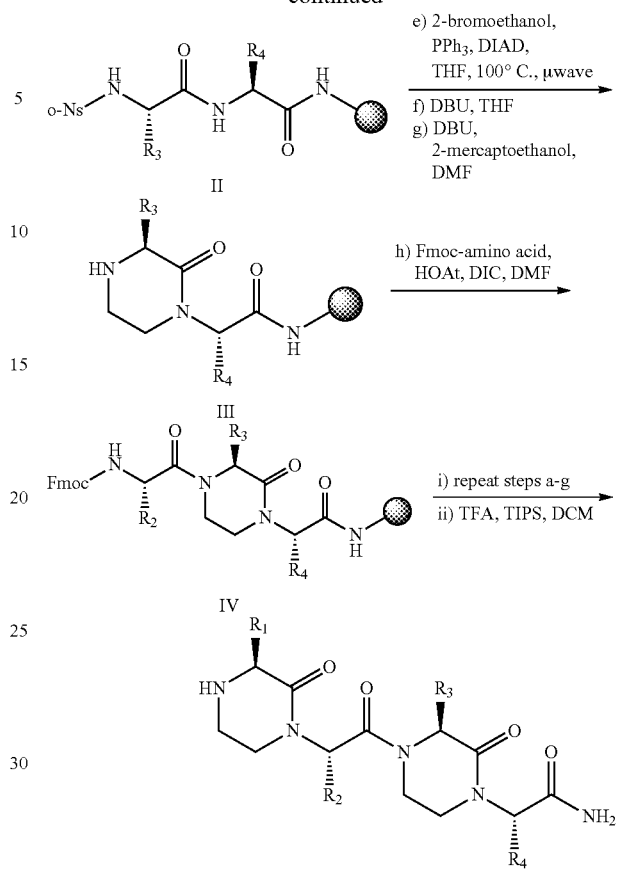

An Fmoc amino acid linked to Wang or Knorr Rink Amide resin (I) was extended to a dipeptide using standard Fmoc solid phase peptide synthesis methods in a solid phase reaction vessel (Coin et al., *Nat. Protoc.* 2:3247 (2007), which is hereby incorporated by reference in its entirety). The resultant dipeptide was deprotected with 20% piperidine/dimethylformamide (DMF) and the resin was washed sequentially with DMF, dichloromethane (DCM), methanol (MeOH), and diethyl ether and dried under vacuum. o-Nitrobenzenesulfonyl chloride (Ns-Cl, 10 eq) and collidine (10 eq) were dissolved in dry DCM and added to the reaction vessel. The mixture was shaken for 2 hours at 23° C. to obtain compound II.

The resin was washed sequentially with DMF, DCM, MeOH, and diethyl ether and dried for 12 hours under vacuum. The resin was transferred to a glass microwave tube (CEM). Triphenylphosphine ($PPh_3$, 10 eq) was added and the tube was flushed with nitrogen gas for 30 minutes. Tetrahydrofuran (THF), diisopropyl azodicarboxylate (DIAD, 10 eq), and 2-bromoethanol (10 eq) were added and the reaction mixture was subjected to microwave irradiation (200 watts, 250 psi) for 10 minutes at 100° C. The resin was washed sequentially with THF, DMF, and DCM. The resin was transferred to a solid phase vessel and treated with 1,8-diazabicyclo[5.4.0]undec-7-ene (DBU) in THF for 2 hours. The resin was washed with THF, DMF, DCM, and diethyl ether and allowed to dry for 30 minutes followed by treatment with DBU and 2-mercaptoethanol in DMF for 2 hours to obtain compound III.

Compound III was then washed with DMF, DCM, MeOH, and diethyl either and dried. The desired pre-activated Fmoc-amino acid was added to the resin and the mixture was shaken at 23° C. for 12 hours affording compound IV.

Nosyl protection and the ring formation steps were repeated to obtain oxopiperazine dimer V after cleavage from the resin with 95% trifluoroacetic acid (TFA), 2.5% water, and 2.5% triisopropylsilane (TIPS).

Oxopiperazines 21-25 were synthesized and characterized by HPLC and $^1$H-NMR. Their structure and $^1$H-NMR characterization values are shown in Table 7 below. HPLC traces are shown in FIGS. 6A-E. Oxopiperazines 26 and 27 were synthesized and characterized as described in International Application No. PCT/US13/26722, which is hereby incorporated by reference in its entirety).

TABLE 7

Compound Characterization

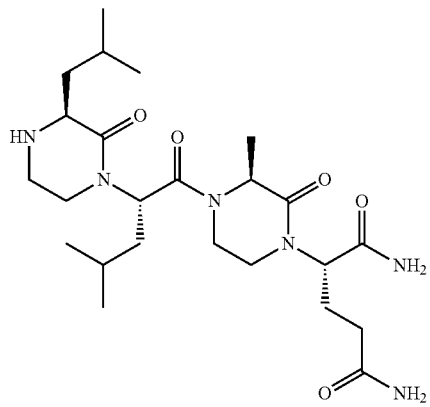 [SMILES: CC(C)C[C@@H]1NCCN([C@@H](CC(C)C)C(=O)N2CCN([C@@H](CCC(N)=O)C(N)=O)C(=O)[C@@H]2C)C1=O]

Oxopiperazine 21: LLAQ-NH$_2$
$^1$H-NMR (600 MHz, d$_6$-DMSO, 100° C.) δ 6.87 (br, 3H), 6.61 (br, 3H), 5.36 (t, J = 7.47, 1H), 4.90-4.85 (m, 1H), 4.67 (q, J = 6.88, 1H), 3.96 (br, 2H), 3.63-3.24 (m, 8H), 1.95-1.82 (m, 3H), 1.72-1.58 (m, 3H), 1.57-1.49 (m, 1H), 1.38 (s, 3H), 1.06-0.75 (m, 12H). HRMS (ESI) C$_{24}$H$_{42}$N$_6$O$_5$ [M + H]$^+$ calc'd = 494.3217; found = 495.3502.
See FIG. 6A.

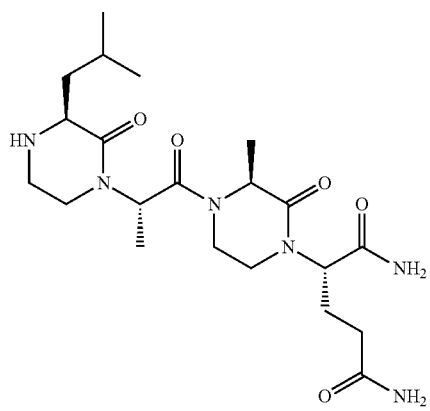 [SMILES: CC(C)C[C@@H]1NCCN([C@@H](C)C(=O)N2CCN([C@@H](CCC(N)=O)C(N)=O)C(=O)[C@@H]2C)C1=O]

Oxopiperazine 22: LAAQ
$^1$H-NMR (400 MHz, d$_6$-DMSO, 100° C.) δ 6.77 (br, 2H), 6.52 (br, 2H), 5.34 (q, J = 6.91, 1H), 4.90-4.84 (m, 1H), 4.67 (q, J = 6.91, 1H), 4.01-3.91 (m, 1H), 3.76-3.69 (m, 1H), 3.57-3.27 (m, 7H), 3.24-3.14 (m, 1H), 2.19-2.01 (m, 3H), 2.00-1.80 (m, 3H), 1.64-1.55 (m, 1H), 1.38 (d, J = 6.92, 3H), 1.27 (d, J = 6.92, 3H), 0.94 (t, J = 6.02, 6H). HRMS (ESI) C$_{21}$H$_{36}$N$_6$O$_5$ [M + H]$^+$ calc'd = 453.2747; found = 453.2863.
See FIG. 6B.

TABLE 7-continued

Compound Characterization

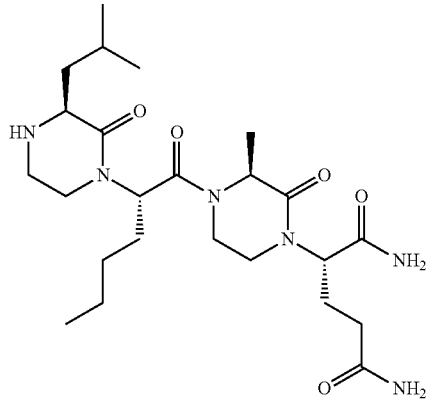 [SMILES: CCCC[C@@H](C(=O)N1CCN([C@@H](CCC(N)=O)C(N)=O)C(=O)[C@@H]1C)N1CCN[C@@H](CC(C)C)C1=O]

Oxopiperazine 23: L(Nle)AQ
$^1$H-NMR (600 MHz, d$_6$-DMSO, 100° C.) δ 6.87 (br, 4H), 5.27 (t, J = 7.25, 1H), 4.92-4.83 (m, 1H), 4.67 (q, J = 7.07, 1H), 3.96 (br, 1H), 3.88 (br, 1H), 3.59-3.56 (m, 1H), 3.54-3.46 (m, 3H), 3.45-3.39 (m, 2H), 3.36-3.31 (m, 1H), 3.30-3.21 (m, 1H), 2.12-2.01 (m, 2H), 1.99-1.83 (m, 2H), 1.80-1.59 (m, 4H), 1.39-1.20 (m, 8H), 0.95 (d, J = 6.29, 3H), 0.94 (d, J = 6.19, 3H), 0.89 (t, J = 7.31, 3H). HRMS (ESI) C$_{24}$H$_{42}$N$_6$O$_5$ [M + H]$^+$ calc'd = 495.3217; found = 495.3377.
See FIG. 6C.

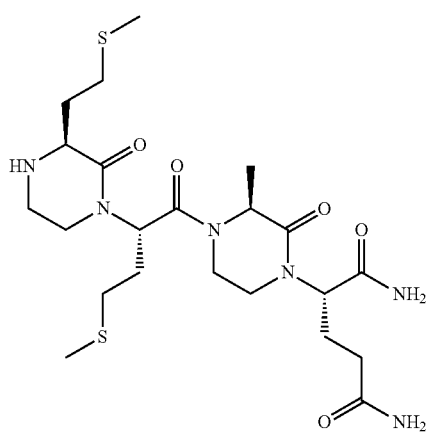 [SMILES: CSCC[C@@H]1NCCN([C@@H](CCSC)C(=O)N2CCN([C@@H](CCC(N)=O)C(N)=O)C(=O)[C@@H]2C)C1=O]

Oxopiperazine 24: MMAQ
$^1$H-NMR (600 MHz, d$_6$-DMSO, 100° C.) δ 9.33 (br, 1H), 6.90 (br, 3H), 5.46 (t, J = 6.91, 1H), 4.91-4.84 (m, 1H), 4.70-4.63 (m, 1H), 4.16-3.91 (m, 1H), 3.87-3.75 (m, 1H), 3.59-3.54 (m, 2H), 3.50 (t, J = 5.98, 2H), 3.47-3.40 (m, 1H), 3.36-3.22 (m, 3H), 2.70-2.60 (m, 3H), 2.23-2.14 (m, 1H), 2.08 (d, J = 2.96, 3H), 2.07-1.87 (m, 5H), 1.74-1.62 (m, 5H), 1.7 (br, 1H), 1.27 (s, 3H). HRMS (ESI) C$_{22}$H$_{38}$N$_6$O$_5$S$_2$ [M + H]$^+$ calc'd = 530.2345; found = 531.2423.
See FIG. 6D.

TABLE 7-continued

Compound Characterization

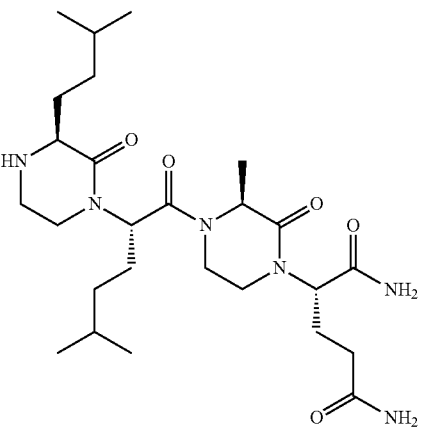 [SMILES: CC(C)CC[C@@H]1NCCN([C@@H](CCC(C)C)C(=O)N2CCN([C@@H](CCC(N)=O)C(N)=O)C(=O)[C@@H]2C)C1=O]

Oxopiperazine 25: (Hle)(Hle)AQ
$^1$H-NMR (600 MHz, d$_6$-DMSO, 100° C.) δ 6.83 (br, 4H), 5.26 (t, J = 7.06, 1H), 4.92-4.83 (m, 1H), 4.66 (q, J = 6.80, 1H), 3.96 (br, 1H), 3.88 (br, 1H), 3.55-3.46 (m, 3H), 3.45-3.36 (m, 3H), 3.35-3.30 (m, 1H), 3.29-3.22 (m, 1H), 3.21 (s, 1H), 1.99-1.83 (m, 2H), 1.83-1.63 (m, 3H), 1.62-1.49 (m, 2H), 1.46-1.20 (m, 7H), 1.19-1.09 (m, 2H), 0.95-0.83 (m, 12H). HRMS (ESI) C$_{24}$H$_{42}$N$_5$O$_5$ [M + H]$^+$ calc'd = 523.3530; found = 523.3642.
See FIG. 6E.

Example 8—Tryptophan Fluorescence Binding Assay

Relative affinities of OHMs for p300-CH1 were determined using a tryptophan fluorescence binding assay. Spectra were recorded on a QuantaMaster 40 spectrofluorometer (Photon Technology International) in a 10 mm quartz fluorometer cell at 25° C. with 4 nm excitation and 4 nm emission slit widths from 200 to 400 nm at intervals of 1 nm/s. Samples were excited at 295 nm and fluorescence emission was measured from 200-400 nm and recorded at 335 nm. OHM stock solutions were prepared in DMSO. Aliquots containing 1 μL DMSO stocks were added to 400 μL of 1 μM p300-CH1 in 50 mM Tris and 100 μM NaCl (pH 8.0). After each addition, the sample was allowed to equilibrate for 5 minutes before UV analysis. Background absorbance and sample dilution effects were corrected by titrating DMSO into p300-CH1 in an analogous manner. Final fluorescence is reported as the absolute value of [(F$_1$-F$_0$)/F$_1$]*100, where F$_1$ is the final fluorescence upon titration, and F$_0$ is the fluorescence of the blank DMSO titration. EC$_{50}$ values for each peptide were determined by fitting the experimental data to a sigmoidal dose-response nonlinear regression model in GraphPad Prism 5.0, and the dissociation constants, K$_D$, were obtained from equation (2).

$$K_D = (R_T \times (1 - F_{SB}) + L_{ST} \times F_{SB}^2)/F_{SB} - L_{ST} \quad (2)$$

where:
R$_T$=Total concentration of p300-CH1
L$_{ST}$=Total concentration of fluorescent peptide
F$_{SB}$=Fraction of bound fluorescent peptide Results and Discussion of Examples 1-8

Protein design is the process of predicting an amino acid sequence that will fold into a desired structure or carry out a desired function (Butterfoss & Kuhlman, *Ann. Rev. Biophys. Biomolec. Struct.* 35:49 (2006), which is hereby incorporated by reference in its entirety). In order to design more potent analogs, a computational approach that combines success in computational protein design (Butterfoss & Kuhlman, *Ann. Rev. Biophys. Biomolec. Struct.* 35:49 (2006); Kuhlman et al., *Science* 302:1364 (2003); Jiang et al., *Science* 319:1387 (2008), each of which is hereby incorporated by reference in its entirety) with peptidomimetic scaffolds was used. Protein design principles to optimize the affinity of oxopiperazine mimetics was achieved using Rosetta (rosettacommons.org) (Leaver-Fay et al., *Methods Enzymol.* 487:545 (2011), which is hereby incorporated by reference in its entirety).

The objective of computational molecular design is to reduce the total number of possible designs to a manageable number that can be efficiently synthesized and experimentally tested. An oxopiperazine dimer has four variable positions and assuming a standard library of 17 amino acids (20 canonical amino acids without Cys, Gly, and Pro), the total number of possible designs would be >83,500. This calculation does not account for noncanonical amino acids, whose inclusion significantly raises the number of potential designs. Experimentally synthesizing and testing this many designs would be prohibitive for academic labs. Rosetta computational design reduces the number of total designs one must synthesize to obtain potent ligands and streamlines the process of finding a high affinity binder.

Figure 7:
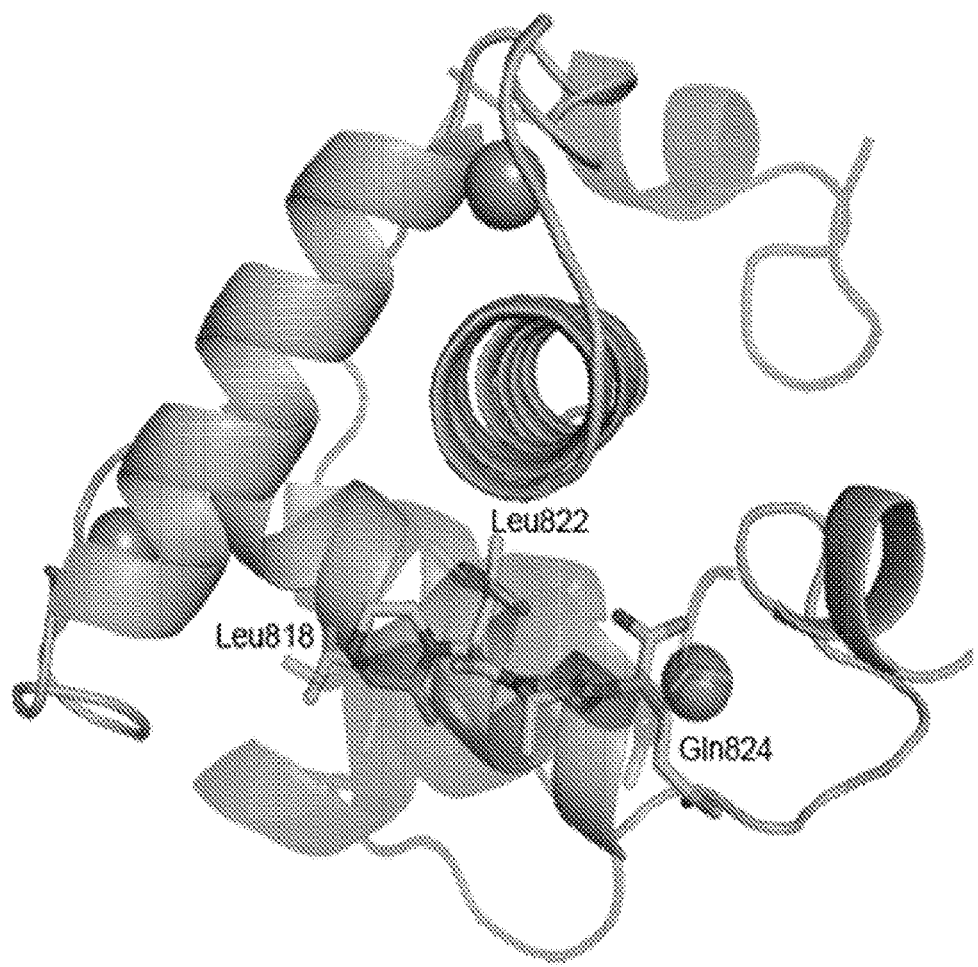
FIG. 7 relates to the design of HIF1α mimetics as ligands for p300-CH1.

A Rosetta oxopiperazine design protocol was recently used to design oxopiperazine helix mimetics that target the p53-Mdm2 interaction (U.S. Provisional Patent Application No. 61/979,784 to Arora et al., which is hereby incorporated by reference in its entirety). To further validate the potential of the Rosetta oxopiperazine design protocol, inhibitors of a different transcriptional complex were developed. It has recently been shown that stabilized peptide helices (Kushal et al., *Proc. Nat'l Acad. Sci. U.S.A.* 110:15602 (2013), which is hereby incorporated by reference in its entirety) and small molecule oxopiperazine analogs (Lau et al., *Proc. Nat'l Acad. Sci.* 10.1073/pnas.1402393111 (published online May 14, 2014), which is hereby incorporated by reference in its entirety) that mimic a key helical domain of HIF1α can inhibit hypoxia inducible signaling in cell culture and animal models. The C-terminal domain of HIF1α utilizes two short α-helices to bind to the CH1 domain of p300/CBP (FIG. 7). Computational alanine scanning (Kortemme et al., *Nat. Struct. Mol. Biol.* 11:371 (2004), which is hereby incorporated by reference in its entirety) studies on the complex reveal that four helical residues from the HIF1α helix$_{816\ 824}$ (Leu818, Leu822, Asp823, and Gln824) make close contacts with the CH1 domain of p300/CBP. Three of these residues, Leu818, Leu822 and Gln824, can be mimicked by oxopiperazine dimers consisting of the appropriate building blocks (FIG. 7). Based on this analysis, analogs of HIF1α were designed to inhibit its binding with p300/CBP. The design and p300/CPB binding properties of oxopiperazine helix mimetics (OHMs) 21-31 are shown in Table 8 below.

TABLE 8

Oxopiperazine HIF Mimics Targeting the CH1 Domain of p300/
CBP-Rosetta Predicted Binding Energy vs. Experimental $K_d$ (nM)

| OHM | $R_1$ | $R_2$ | $R_3$ | $R_4$ | Kd (μM)[a] | R.E.U.[b] |
|---|---|---|---|---|---|---|
| 21 | Leu | Leu | Ala | Gln | 0.53 ± 0.14 | 10.1 |
| 22 | Leu | Ala | Ala | Gln | >10 | 11.4 |
| 23 | Leu | Nle | Ala | Gln | 0.03 ± 0.01 | 5.34 |
| 24 | Met | Met | Ala | Gln | 0.24 ± 0.04 | 10.3 |
| 25 | Hle | Hle | Ala | Gln | 0.16 ± 0.06 | 5.80 |
| 26 | Leu | Leu | Ala | Ala | 0.62 ± 0.27 | 10.2 |
| 27 | Ala | Ala | Ala | Ala | >10 | 11.7 |
| 28 | Hle | Leu | Ala | Gln | ND[c] | 10.4 |
| 29 | Met | Leu | Ala | Gln | ND[c] | 11.9 |
| 30 | Leu | Hle | Ala | Gln | ND[c] | 6.42 |
| 31 | Hle | Nle | Ala | Gln | ND[c] | 9.63 |

[a]Binding affinity for p300-CH1 was determined using an intrinsic tryptophan fluorescence assay.
[b]Rosetta predicted binding energy.
[c]ND = Not determined. OHMs 28-31 were not synthesized, but are expected to bind to p300/CPB as well as or better than OHM 21.

OHM 21 contains projections representing all three wild-type residues from HIF1α: $R_1$ as Leu818, $R_2$ as Leu822, and $R_4$ as Gln824 (Table 8). The $R_3$ position of the oxopiperazine scaffold was not predicted to make contacts with the target protein; an alanine residue was inserted at this position. OHM 22 was designed as a single mutant of OHM 21 with the $R_2$ position substituted with an alanine residue.

Results with OHMs 21 and 22 have been previously described (Lau et al., *Proc. Nat'l Acad. Sci.* 10.1073/pnas.1402393111 (published online May 14, 2014); International Application No. PCT/US13/26722 to Arora et al.; Bullock Lau et al., *Proc. Nat'l Acad. Sci.* 10.1073/pnas.1402393111 (published online May 14, 2014), each of which is hereby incorporated by reference in its entirety)). Oxopiperazine 21, consisting of the wild-type residues, bound the CH1 domain of p300 with an affinity of 533±24 nM; whereas, the negative control OHM 22 displayed a very weak affinity for p300-CH1, with a $K_d$ value of >30 μM (Table 8 and FIG. 8). The binding affinities of OHMs 21-25 for p300-CH1 were evaluated using intrinsic tryptophan fluorescence spectroscopy (Kushal et al., *Proc. Nat'l Acad. Sci. U.S.A.* 110:15602 (2013); Dial et al., *Biochemistry* 42:9937 (2003), each of which is hereby incorporated by reference in its entirety). Because Trp403 lies in the binding cleft of p300/CBP where a native HIF1α$_{816-824}$ helix binds, it offers a probe for investigating mimetics of this helix. As part of this earlier study, the interaction of OHM 21 with the p300-CH1 domain was also characterized using $^1$H-$^{15}$N HSQC NMR titration experiments with the uniformly $^{15}$N-labeled CH1. Addition of OHM 21 led to consistent shifts in resonances of residues corresponding to the HIF1α$_{816-824}$ binding pocket. OHM 21 efficiently downregulated HIF signaling in cell culture at micromolar levels and reduced tumor levels in triple-negative breast cancer cell line MDA-MB-231 mouse xenograft models. Importantly, microarray gene expression profiling data showed that the designed oxopiperazine helix mimetic, despite its low molecular weight and a limited number of contacts with the intended target protein, shows high specificity on a genome-wide scale.

The encouraging results with OHM 21 provided a platform to test the potential of the Rosetta peptidomimetic design strategy to design further HIF mimetics with improved functionality. Whether the computational approach could rapidly suggest nonnatural residues that may boost the binding affinity for p300-CH1 was examined. The p300/OHM 21 binding was analyzed using the established protocol, with a library of noncanonical amino acids (Table 6, supra). The computational predictions suggested that inclusion of longer aliphatic side chains in place of the isobutyl group of leucine would lead to better contacts with the hydrophobic pocket. Specifically, substitution with non-natural side chains at the $R_2$ position of OHM 21 was predicted to lead to an optimized binder (FIGS. 9A-D).

Figure 5:
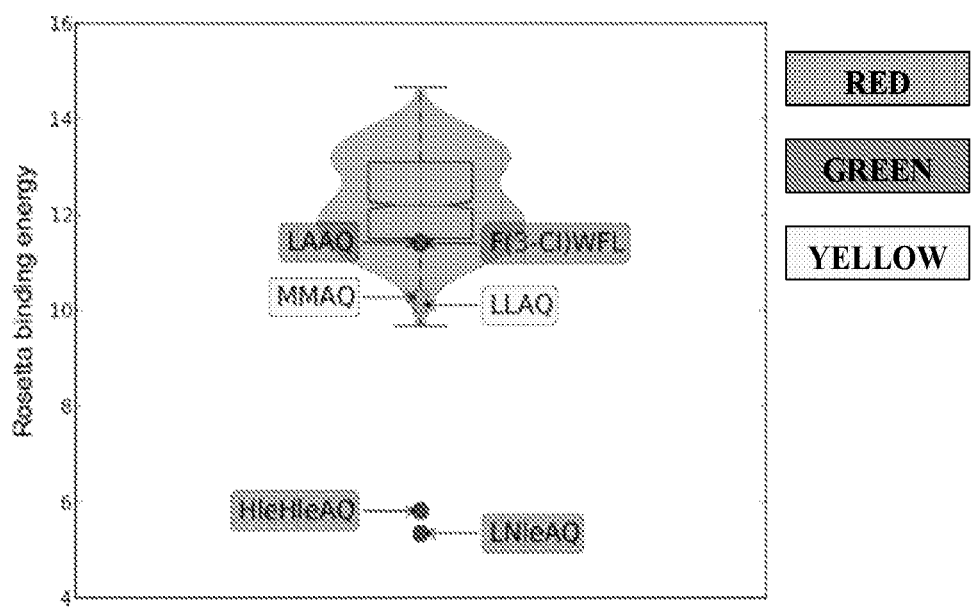
FIG. 5 is a violin plot showing distribution of the predicted oxopiperazine analogs for their potential to target the CH1 domain of p300/CBP. The binding affinity is expressed as Rosetta binding energy unit (REU). The plot shows the energy scores for the top scoring 1,000 designs selected from 30,000 random Rosetta designs (gray violin) as well as experimentally tested designs (dots). The Rosetta score discriminates between good binders (green and yellow label) and weak binders (red label).
Figure 6A:
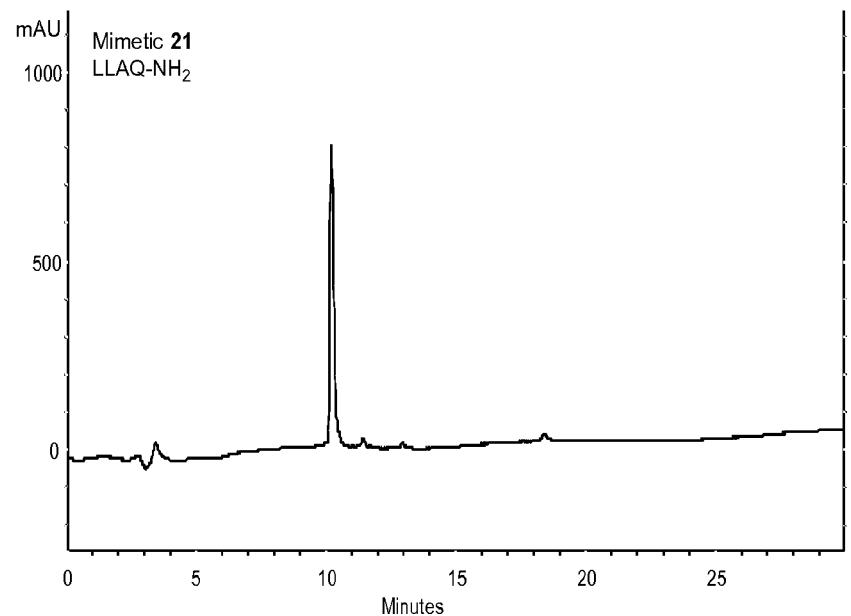
FIGS. 6A-E are analytical HPLC traces of the indicated oxopiperazines and monomer-peptides. For compound 21, HPLC was performed in 5% to 95% acetonitrile in water (0.1% formic acid) for 30 minutes. The UV trace is at 220 nm. For compound 22, HPLC was performed in 5% to 95% acetonitrile in water (0.1% trifluoroacetic acid) for 10 minutes; 95% to 100% from 10-15 minutes. The UV trace is at 230 nm. For compounds 23-25, HPLC was performed in 5% to 95% acetonitrile in water (0.1% trifluoroacetic acid) for 10 minutes. The UV traces are at 220 nm.
Figure 6B:
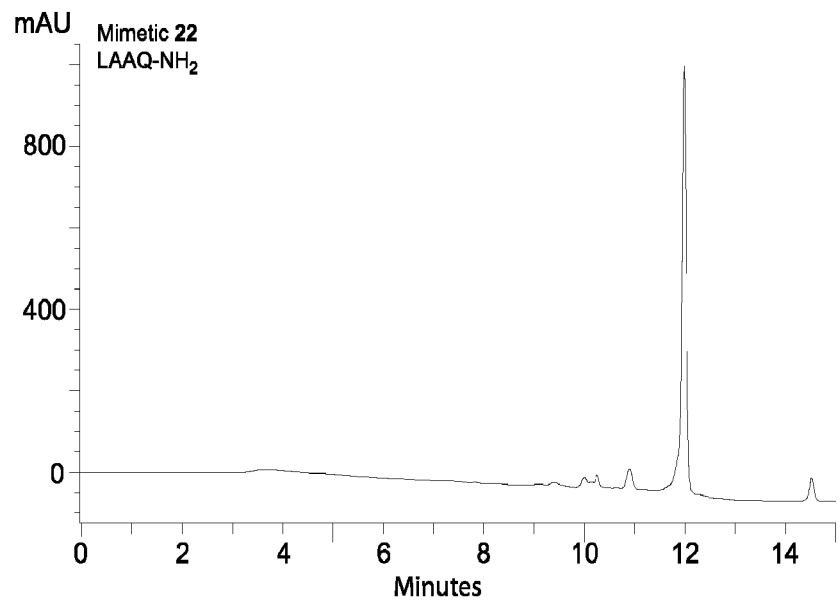
Figure 6C:
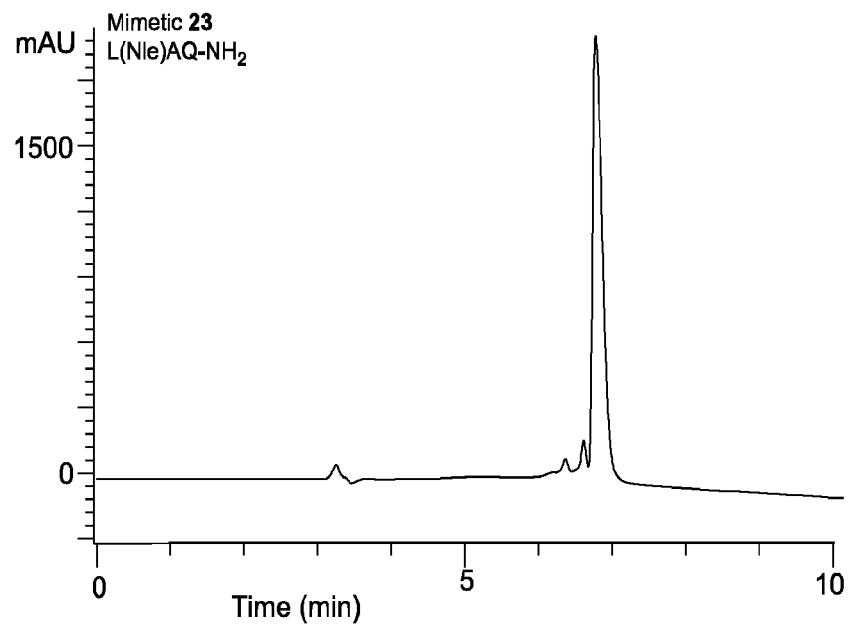
Figure 6D:
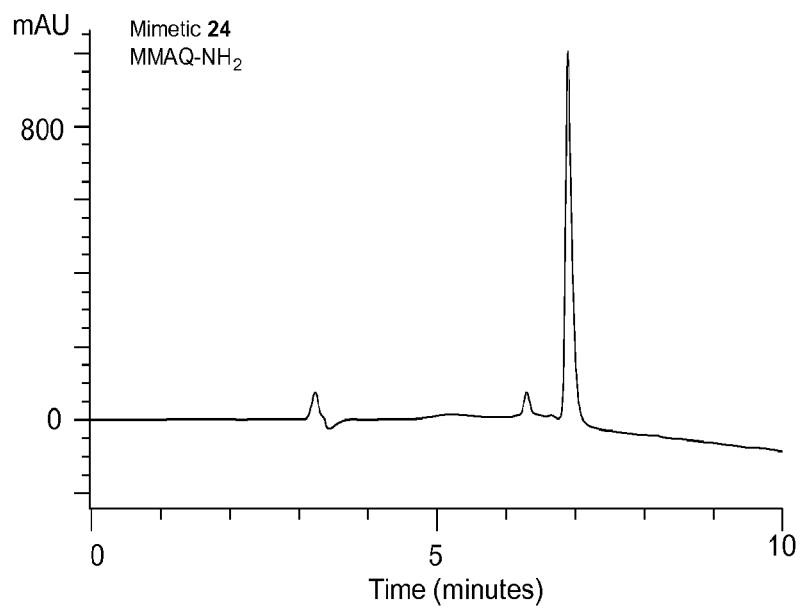
Figure 6E:
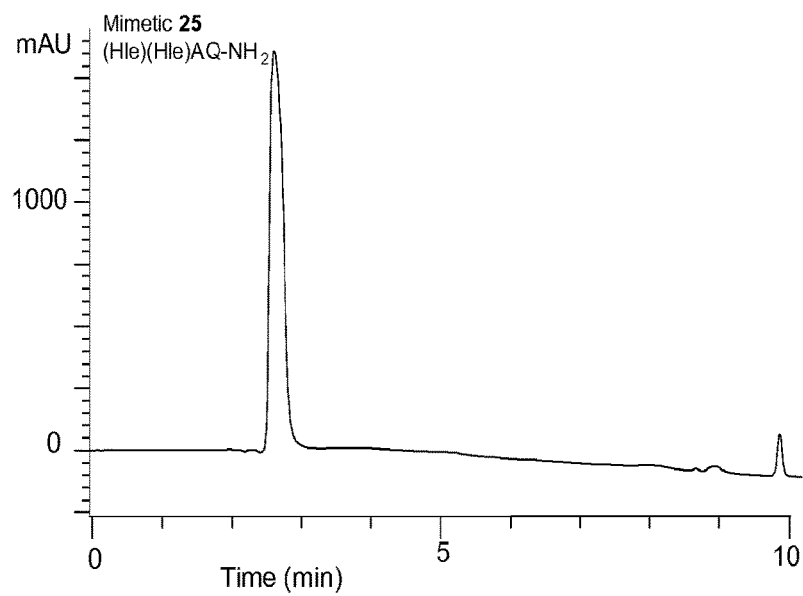

FIG. 5 shows a violin plot for OHMs targeting the CH1 domain. The gray area represents the top 1000 scores from Rosetta's evaluation of 30,000 designs. The predicted high affinity designs feature norleucine (Nle) and homoleucine (Hle) residues in place of the wild-type leucine analogs and are substantially lower in energy than the rest of the sequences tested by Rosetta. Substitution of the two leucine residues with methionines was predicted to be less effective than with noncanonical residues, suggesting that space-filling and polarity of side chain groups are necessary for optimal results. Other combinations of homoleucine, norleucine, and leucine residues were also examined (see Table 8, supra).

To experimentally evaluate the predictions, three analogs were prepared representing top designs in which both leucine groups of OHM 21 were substituted with methionine, norleucine, or homoleucine to obtain OHMs 23-25 (Table 8, supra). Each of these compounds bound p300 with higher affinity than the parent OHM 21, with OHM 23 providing a 13-fold enhancement in binding affinity ($K_d$=30.2±1.87 nM).

A strong correlation was found between the experimental results for p300/CBP and Rosetta predictions (FIG. 10 and Table 8), further highlighting the success of the computational design protocol. Since the fluorescence-binding assay uses a native tryptophan residue in the target molecular pocket, it provides a stringent test for the binding site specificity. Characterization of the interaction of OHM 21 with p300-CH1 domain using $^1$H-$^{15}$N HSQC NMR titration experiments further confirms the target pocket for the designed analogs.

Example 9—Cross-Specificities of the Designed Compounds for Mdm2 and p300

Analyses of protein-protein interaction (PPI) networks suggest that the human interactome consists of hundreds of thousands of different PPIs (Bonetta, *Nature* 468:851 (2010); Venkatesan et al., *Nat. Meth.* 6:83 (2009), each of which is hereby incorporated by reference in its entirety). Analysis of the high-resolution protein complexes available in the Protein Data Bank reveals that up to 60% of such protein complexes contain an interfacial α-helix (Bullock et al., *J. Am. Chem. Soc.* 133:14220 (2011); Jochim & Arora, *ACS Chem. Biol.* 5:919 (2010); Jochim & Arora, *Mol. BioSyst.* 5:924 (2009), each of which is hereby incorporated by reference in its entirety). Thus, a central question in the design of helix mimetics as PPI inhibitors pertains to their specificity on the genome-wide scale. The specificity of OHM 21, designed to be a transcriptional inhibitor for off-target regulation, was recently probed using the Affymetrix Human Gene ST 1.0 arrays containing oligonucleotide sequences representing over 28,000 transcripts (Lau et al., *Proc. Nat'l Acad. Sci.* 10.1073/pnas.1402393111 (published online May 14, 2014), which is hereby incorporated by reference in its entirety). This compound was found to be remarkably specific given the limited number of contacts it offers.

Figure 12:
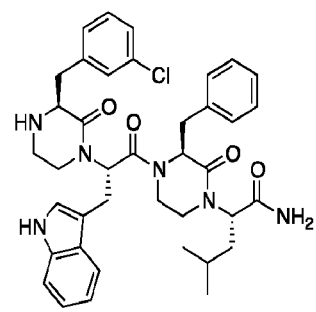
FIG. 12 shows the structure of p53 mimic OHM 18.

As described herein, potent small molecule helix mimetics that feature noncanonical side chains have been computationally designed as potential inhibitors of protein-protein interactions. Oxopiperazine mimics of p53 that inhibit the p53-Mdm2 interaction are described in U.S. Provisional Patent Application No. 61/979,784 to Arora et al., which is hereby incorporated by reference in its entirety. As a preliminary analysis of Rosetta's ability to predict the specificity of OHMs against unintended targets, the binding affinity of HIF mimics OHM 23 and OHM 25 against Mdm2 (Table 9 and FIG. 11A), and that of p53 mimic OHM 18 (see FIG. 12) against p300-CH1 (Table 9 and FIG. 11B), were determined.

TABLE 9

Cross-Specificities of Oxopiperazine p53 and HIF Mimics Against p300-CH1 and Mdm2.

| Ligand | p300 $K_d$ (μM)[a] | Mdm2 $K_d$ (μM)[b] |
|---|---|---|
| 18 | >30 | 0.3 ± 0.04 |
| 23 | 0.03 ± 0.01 | >50 |
| 25 | 0.16 ± 0.06 | >50 |

[a] Binding affinity for p300-CH1 was determined using an intrinsic tryptophan fluorescence assay.
[b] Binding affinity for Mdm2 was determined using a competitive fluorescence polarization assay with Flu-p53 as a probe (see U.S. Provisional Application No. 61/979,784 to Arora et al., which is hereby incorporated by reference in its entirety).

Figure 13:
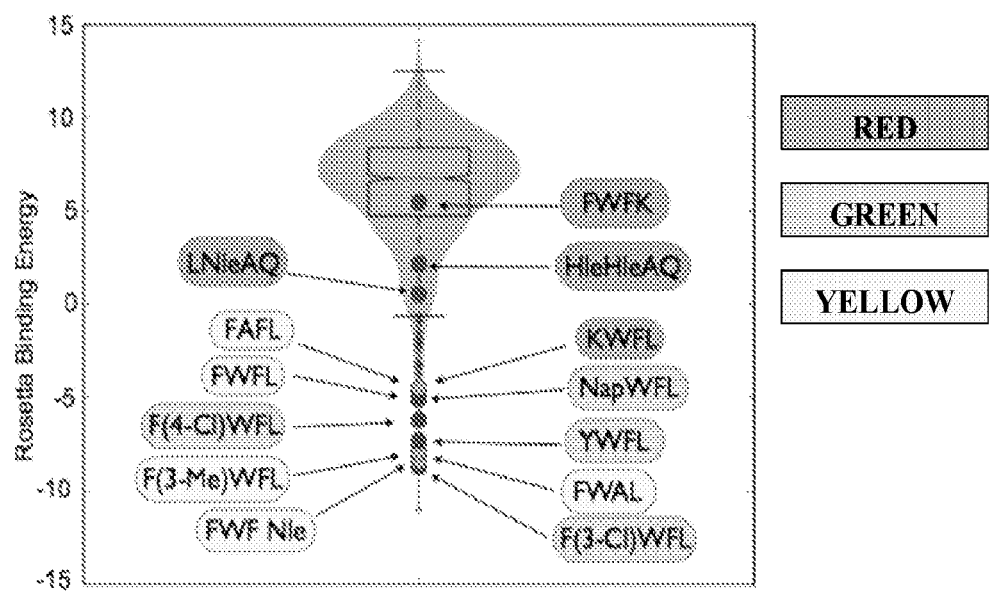
FIG. 13 is a violin plot showing the distribution of the predicted oxopiperazine analogs for their potential to target Mdm2. The binding affinity is expressed as Rosetta binding energy unit (REU). The plot shows the energy scores for the top scoring 1,000 designs selected from 30,000 random Rosetta designs (gray violin) as well as experimentally tested designs (dots). The Rosetta score discriminates between good binders (green and yellow label) and weak binders (red label).

These analogs were chosen because they represent the highest affinity ligands obtained for their respective targets and contain noncanonical residues. Calculations with the modified version of Rosetta, described above, predict that the p53 mimic OHM 18 is a poor ligand for p300-CH1 and that HIF mimetics OHM 23 and OHM 25 are not optimal designs for Mdm2. Specifically, the calculated Rosetta binding energy (R.E.U.) for OHM 18/p300-CH1 binding is the same as that calculated for OHM 22, a negative control designed for the HIF/p300 interaction (FIG. 5). Likewise, Rosetta predicts compounds OHM 23 and OHM 25 to have a high-energy interaction with Mdm2; >6 R.E.U.'s when compared to OHM 18, the high affinity Mdm2 ligand (FIG. 13). These predictions were confirmed in experimental binding assays.

The binding of oxopiperazine derivatives was tested using the assays described above. As expected, the compounds are specific for their cognate receptors (Table 9, supra), with each showing more than 100-fold specificity for the desired protein surface. These results provide support for the hypotheses that the computational strategy described herein can be used to ultimately predict specificity of the designed peptidomimetics on the genome-wide scale.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An oxopiperazine selected from the group consisting of
(i) Formula IA:

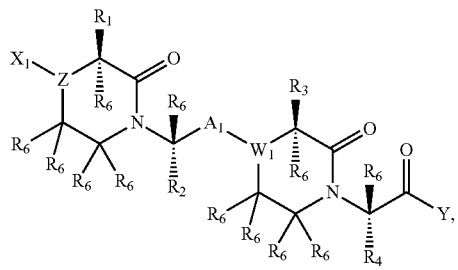

wherein:

$R_1$ is hydrophobic and is an amino acid side chain, OR, SR, an alkyl, or an aryl; wherein R is independently H, an alkyl, or an aryl;

$R_2$ is an amino acid side chain, OR, SR, an alkyl, or an aryl; wherein R is independently H, an alkyl, or an aryl; wherein $R_2$ is either a leucine side chain or $R_2$ is longer than a leucine side chain by at least one backbone methylene; and with the proviso that $R_1$ and $R_2$ are not both an aryl;

$R_3$ is hydrophobic and is an amino acid side chain, SR, or an alkyl; wherein R is independently H, an alkyl, or an aryl;

$R_4$ is a hydrogen bond donor, a hydrophobic amino acid side chain, or an amide;

each $R_6$ is independently H, $N(R)_2$, OR, halogen, an alkyl, or an aryl; wherein each R is independently H, an alkyl, or an aryl;

$X_1$ is H, $N(R)_2$, OR, COR', $CO_2R'$, CONR', an alkyl, an aryl, an arylalkyl, a cycloalkyl, a heteroaryl, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag;

Z is N;

$A_1$-$W_1$ is:

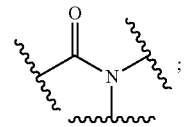 [SMILES: *C(=O)N(*)*]

and

Y is OR', $N(R''')_2$, an alkyl, an aryl, an arylalkyl, a cycloalkyl, a heteroaryl, an amino acid, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag;

and wherein each R''' is independently H, CO₂R', CONR', an alkyl, an aryl, an arylalkyl, a cycloalkyl, a heteroaryl, a targeting moiety, or a tag;
and (ii) Formula IB:

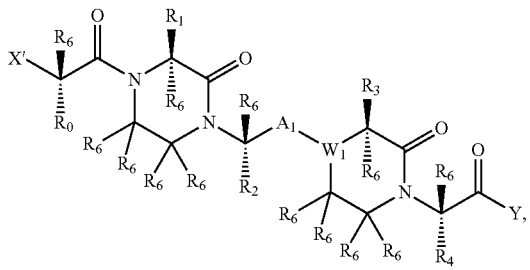

wherein:
$R_0$ is hydrophobic and is an amino acid side chain, OR, SR, an alkyl, or an aryl; wherein R is independently H, an alkyl, or an aryl;
$R_1$ and $R_2$ are each independently a solubilizing group, a hydrophobic amino acid side chain, H, $N(R)_2$, OR, SR, halogen, an alkyl, or an aryl; wherein each R is independently H, an alkyl, or an aryl;
$R_3$ is an amino acid side chain, OR, SR, an alkyl, or an aryl; wherein R is independently H, an alkyl, or an aryl; wherein $R_3$ is either a leucine side chain or $R_3$ is longer than a leucine side chain by at least one backbone methylene; and with the proviso that $R_0$ and $R_3$ are not both an aryl;
$R_4$ is a hydrogen bond donor, a hydrophobic amino acid side chain, or an amide;
each $R_6$ is independently H, $N(R)_2$, OR, halogen, an alkyl, or an aryl; wherein each R is independently H, an alkyl, or an aryl;
X' is H, COR', CO₂R', CONR', OR', $N(R'')_2$, an alkyl, an aryl, an arylalkyl, a cycloalkyl, a heteroaryl, a solubilizing group, a targeting moiety, or a tag; wherein R' is H, an alkyl, an aryl, an arylalkyl, a cycloalkyl, a heteroaryl, an amino acid residue, a peptide of 1 to about 10 amino acid residues, a targeting moiety, or a tag; and wherein each R'' is independently H, CO₂R', CONR', an alkyl, an aryl, an arylalkyl, a cycloalkyl, a heteroaryl, a targeting moiety, or a tag;
$A_1$-$W_1$ is:

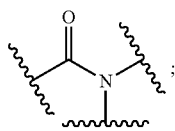 [SMILES: *C(=O)N(*)*]

and
Y is OR', $N(R''')_2$, an alkyl, an aryl, an arylalkyl, a cycloalkyl, a heteroaryl, an amino acid, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, CO₂R', CONR', an alkyl, an aryl, an arylalkyl, a cycloalkyl, a heteroaryl, a targeting moiety, or a tag;

with the proviso that the oxopiperazine is not one of the following compounds

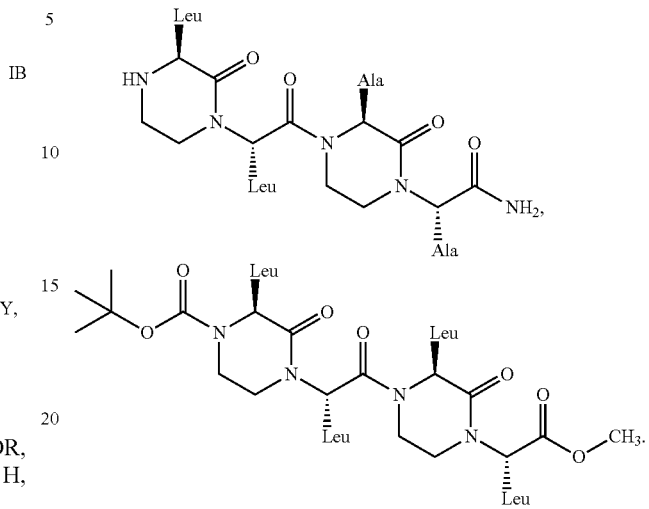

2. The oxopiperazine according to claim 1, wherein the oxopiperazine has a formula of Formula IA.

3. The oxopiperazine according to claim 2, wherein $R_1$ is OR, SR, a $C_3$-$C_6$ alkyl, an aryl, or a side chain of an amino acid selected from the group consisting of leucine, methionine, and homoleucine; $R_2$ is OR, SR, a $C_3$-$C_6$ alkyl, an aryl, or a side chain of an amino acid selected from the group consisting of norleucine, methionine, leucine, and homoleucine; $R_3$ is SR, a $C_1$-$C_3$ alkyl, or a side chain of an amino acid selected from the group consisting of glycine and alanine; $R_4$ is a side chain of an amino acid selected from the group consisting of glutamine, alanine, valine, asparagine, serine, and homoserine; and Y is OH, OR', NEM', $NR'_2$, or $NH_2$.

4. The oxopiperazine according to claim 1, wherein the oxopiperazine has a formula of Formula M.

5. The oxopiperazine according to claim 4, wherein $R_0$ is OR, SR, a $C_3$-$C_6$ alkyl, an aryl, or a side chain of an amino acid selected from the group consisting of leucine, methionine, and homoleucine; $R_3$ is OR, SR, a $C_3$-$C_6$ alkyl, an aryl, or a side chain of an amino acid selected from the group consisting of norleucine, methionine, leucine, and homoleucine; $R_4$ is a side chain of an amino acid selected from the group consisting of glutamine, alanine, valine, asparagine, serine, and homoserine; and Y is OH, OR', NHR', $NR'_2$, or $NH_2$.

6. The oxopiperazine according to claim 1, wherein the oxopiperazine is selected from the group consisting of oxopiperazine helix mimetic ("OHM") 23, OHM 24, OHM 25, OHM 28, OHM 29, OHM 30, and OHM 31:

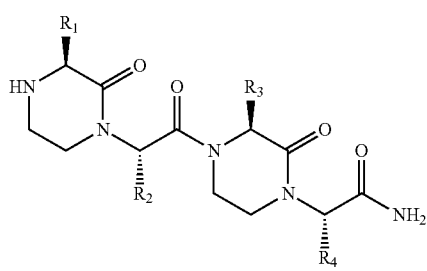

OHM 23: $R_1$=Leu, $R_2$=Nle, $R_3$=Ala, $R_4$=Gln;
OHM 24: $R_1$=Met, $R_2$=Met, $R_3$=Ala, $R_4$=Gln;

OHM 25: R₁=Hle, R₂=Hle, R₃=Ala, R₄=Gln;
OHM 28: R₁=Hle, R₂=Leu, R₃=Ala, R₄=Gln;
OHM 29: R₁=Met, R₂=Leu, R₃=Ala, R₄=Gln;
OHM 30: R₁=Leu, R₂=Hle, R₃=Ala, R₄=Gln;
OHM 31: R₁=Hle, R₂=Nle, R₃=Ala, R₄=Gln.

7. The oxopiperazine according to claim 1, with the proviso that the oxopiperazine is not OHM 21:

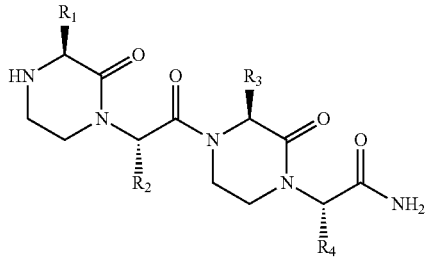

OHM 21: R₁=Leu, R₂=Leu, R₃=Ala, R₄=Gln.

8. A pharmaceutical formulation comprising:
an oxopiperazine according to claim 1 and
a pharmaceutically acceptable vehicle.

9. The pharmaceutical formulation according to claim 8, wherein the oxopiperazine has a formula of Formula IA.

10. The pharmaceutical formulation according to claim 9, wherein $R_1$ is OR, SR, a $C_3$-$C_6$ alkyl, an aryl, or a side chain of an amino acid selected from the group consisting of leucine, methionine, and homoleucine; $R_2$ is OR, SR, a $C_3$-$C_6$ alkyl, an aryl, or a side chain of an amino acid selected from the group consisting of norleucine, methionine, leucine, and homoleucine; $R_3$ is SR, a $C_1$-$C_3$ alkyl, or a side chain of an amino acid selected from the group consisting of glycine and alanine; $R_4$ is a side chain of an amino acid selected from the group consisting of glutamine, alanine, valine, asparagine, serine, and homoserine; and Y is OH, OR', NEM', NR'$_2$, or NH$_2$.

11. The pharmaceutical formulation according to claim 8, wherein the oxopiperazine has a formula of Formula IB.

12. The pharmaceutical formulation according to claim 11, wherein $R_0$ is OR, SR, a $C_3$-$C_6$ alkyl, an aryl, or a side chain of an amino acid selected from the group consisting of leucine, methionine, and homoleucine; $R_3$ is OR, SR, a $C_3$-$C_6$ alkyl, an aryl, or a side chain of an amino acid selected from the group consisting of norleucine, methionine, leucine, and homoleucine; $R_4$ is a side chain of an amino acid selected from the group consisting of glutamine, alanine, valine, asparagine, serine, and homoserine; and Y is OH, OR', NEM', NR'$_2$, or NH$_2$.

13. The pharmaceutical formulation according to claim 8, wherein the oxopiperazine is selected from the group consisting of oxopiperazine helix mimetic ("OHM") 23, OHM 24, OHM 25, OHM 28, OHM 29, OHM 30, and OHM 31:

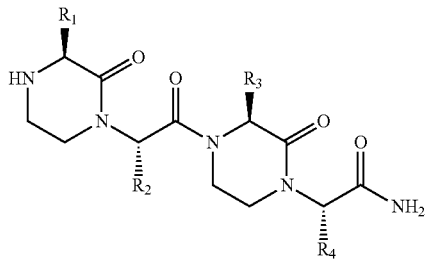

OHM 23: R₁=Leu, R₂=Nle, R₃=Ala, R₄=Gln;
OHM 24: R₁=Met, R₂=Met, R₃=Ala, R₄=Gln;
OHM 25: R₁=Hle, R₂=Hle, R₃=Ala, R₄=Gln;
OHM 28: R₁=Hle, R₂=Leu, R₃=Ala, R₄=Gln;
OHM 29: R₁=Met, R₂=Leu, R₃=Ala, R₄=Gln;
OHM 30: R₁=Leu, R₂=Hle, R₃=Ala, R₄=Gln;
OHM 31: R₁=Hle, R₂=Nle, R₃=Ala, R₄=Gln.

14. The pharmaceutical formulation according to claim 8, with the proviso that the oxopiperazine is not OHM 21:

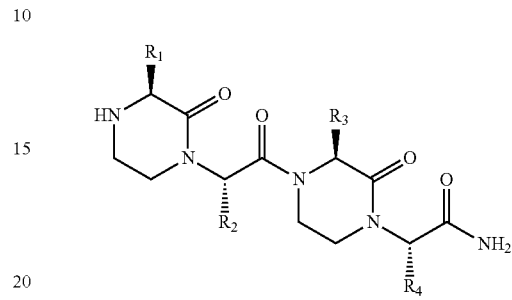

OHM 21: R₁=Leu, R₂=Leu, R₃=Ala, R₄=Gln.

15. A method of reducing transcription of a gene in a cell, wherein transcription of the gene is mediated by interaction of Hypoxia-Inducible Factor 1α with CREB-binding protein and/or p300, said method comprising:
contacting the cell with an oxopiperazine according to claim 1 under conditions effective to reduce transcription of the gene.

16. A method of treating in a subject a disorder mediated by interaction of Hypoxia-Inducible Factor 1α with CREB-binding protein and/or p300, said method comprising:
administering to the subject an oxopiperazine according to claim 1 under conditions effective to treat the disorder.

17. A method of reducing angiogenesis in a tissue, said method comprising:
contacting the tissue with an oxopiperazine according to claim 1 under conditions effective to reduce angiogenesis in the tissue.

18. A method of inducing apoptosis of a cell, said method comprising:
contacting the cell with an oxopiperazine according to claim 1 under conditions effective to induce apoptosis of the cell.

19. A method of decreasing survival and/or proliferation of a cell, said method comprising:
contacting the cell with an oxopiperazine according to claim 1 under conditions effective to decrease survival and/or proliferation of the cell.

20. An oxopiperazine of Formula IC:

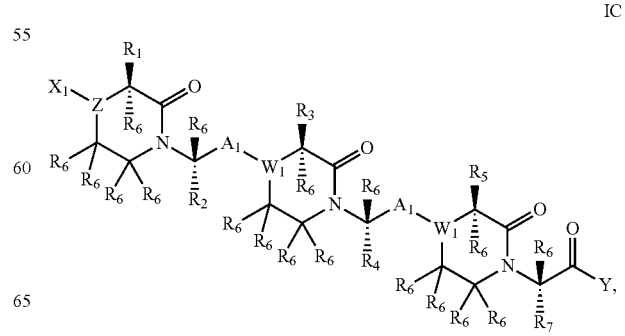

IC wherein:

$R_1$ is hydrophobic and is an amino acid side chain, OR, SR, an alkyl, or an aryl; wherein R is independently H, an alkyl, or an aryl;

$R_2$ is an amino acid side chain, OR, SR, an alkyl, or an aryl; wherein R is independently H, an alkyl, or an aryl; wherein $R_2$ is either a leucine side chain or $R_2$ is longer than a leucine side chain by at least one backbone methylene; and with the proviso that $R_1$ and $R_2$ are not both an aryl;

$R_3$ is hydrophobic and is an amino acid side chain, SR, or an alkyl; wherein R is independently H, an alkyl, or an aryl;

$R_4$ is a hydrogen bond donor or an amide;

$R_5$ is a hydrophobic amino acid side chain;

each $R_6$ is independently H, $N(R)_2$, OR, halogen, an alkyl, or an aryl; wherein each R is independently H, an alkyl, or an aryl;

$R_7$ is a solubilizing group, a hydrophobic amino acid side chain, H, $N(R)_2$, OR, SR, halogen, an alkyl, or an aryl; wherein each R is independently H, an alkyl, or an aryl;

$X_1$ is H, $N(R)_2$, OR, COR', $CO_2R'$, CONR', an alkyl, an aryl, an arylalkyl, a cycloalkyl, a heteroaryl, a peptide of 1 to about 10 amino acid residues, a protecting group for protection of an amine, a solubilizing group, a targeting moiety, or a tag; wherein each R is independently H, an alkyl, or an aryl; and wherein R' is H, an alkyl, an aryl, an arylalkyl, a cycloalkyl, a heteroaryl, a targeting moiety, or a tag;

Z is N;

each $A_1$-$W_1$ is:

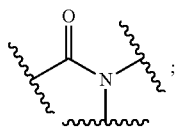 [SMILES: *C(=O)N(*)*]

and

Y is OR', $N(R''')_2$, an alkyl, an aryl, an arylalkyl, a cycloalkyl, a heteroaryl, an amino acid, a peptide of 1 to about 10 amino acid residues, a protecting group for protection of a carboxylic acid, a targeting moiety, or a tag; wherein R' is H, an alkyl, an aryl, an arylalkyl, a cycloalkyl, a heteroaryl, a targeting moiety, or a tag; and wherein each R''' is independently H, $CO_2R'$, CONR', an alkyl, an aryl, an arylalkyl, a cycloalkyl, a heteroaryl, a targeting moiety, or a tag.

21. The oxopiperazine according to claim 20, wherein $R_1$ is OR, SR, a $C_3$-$C_6$ alkyl, an aryl, or a side chain of an amino acid selected from the group consisting of leucine, methionine, and homoleucine; $R_2$ is OR, SR, a $C_3$-$C_6$ alkyl, an aryl, or a side chain of an amino acid selected from the group consisting of norleucine, methionine, leucine, and homoleucine; $R_4$ is a side chain of an amino acid selected from the group consisting of glutamine, asparagine, and homoserine; $R_5$ is a side chain of an amino acid selected from the group consisting of alanine, valine, and serine; and Y is OH, OR', NEM', NR'2, or $NH_2$.

22. A pharmaceutical formulation comprising:
an oxopiperazine according to claim 20 and
a pharmaceutically acceptable vehicle.

23. The pharmaceutical formulation according to claim 22, wherein $R_1$ is OR, SR, a $C_3$-$C_6$ alkyl, an aryl, or a side chain of an amino acid selected from the group consisting of leucine, methionine, and homoleucine; $R_2$ is OR, SR, a $C_3$-$C_6$ alkyl, an aryl, or a side chain of an amino acid selected from the group consisting of norleucine, methionine, leucine, and homoleucine; $R_4$ is a side chain of an amino acid selected from the group consisting of glutamine, asparagine, and homoserine; $R_5$ is a side chain of an amino acid selected from the group consisting of alanine, valine, and serine; and Y is OH, OR', NEM', $NR'_2$, or $NH_2$.

* * * * *